US011826541B2

(12) United States Patent
Cowan et al.

(10) Patent No.: US 11,826,541 B2
(45) Date of Patent: Nov. 28, 2023

(54) SLIDING SYRINGE CAP FOR SEPARATE FILLING AND DELIVERY

(71) Applicant: BAYER HEALTHCARE LLC, Whippany, NJ (US)

(72) Inventors: Kevin Cowan, Allison Park, PA (US); Michael Spohn, Fenelton, PA (US); Barry Tucker, Verona, PA (US); Matthew Walker, Lillington, NC (US); James Dedig, Pittsburgh, PA (US); James Fentress, Creedmoor, NC (US); Joseph Ranaletta, Greenville, SC (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 648 days.

(21) Appl. No.: 16/621,809

(22) PCT Filed: Sep. 12, 2018

(86) PCT No.: PCT/US2018/050640
§ 371 (c)(1),
(2) Date: Dec. 12, 2019

(87) PCT Pub. No.: WO2019/055497
PCT Pub. Date: Mar. 21, 2019

(65) Prior Publication Data
US 2020/0171234 A1 Jun. 4, 2020

Related U.S. Application Data

(60) Provisional application No. 62/575,062, filed on Oct. 20, 2017, provisional application No. 62/558,012, filed on Sep. 13, 2017.

(51) Int. Cl.
*A61M 5/00* (2006.01)
*A61M 5/20* (2006.01)
(Continued)

(52) U.S. Cl.
CPC ............ *A61M 5/007* (2013.01); *A61M 5/204* (2013.01); *A61M 5/3134* (2013.01);
(Continued)

(58) Field of Classification Search
CPC .. A61M 5/204; A61M 5/007; A61M 5/16809; A61M 2005/3104;
(Continued)

(56) References Cited

U.S. PATENT DOCUMENTS 352,715 A 11/1886 Sandmark
798,093 A 8/1905 Edward
(Continued)

FOREIGN PATENT DOCUMENTS

CN 103917269 A 7/2014
EP 1086661 A2 3/2001
(Continued)

OTHER PUBLICATIONS

"International Preliminary Report on Patentability on PCT Application No. PCT/US2018/050640", dated Mar. 26, 2020.

*Primary Examiner* — Nilay J Shah
(74) *Attorney, Agent, or Firm* — David Schramm; Joseph L. Kent; James R. Stevenson

(57) ABSTRACT

A cap for intake and delivery of a fluid from a syringe is described. The cap includes an outer cap assembly comprising a fluid inlet path and a fluid outlet path and an inner cap assembly configured for insertion into a fluid nozzle of the syringe and to provide selective fluid communication between an interior of a syringe and the fluid inlet path or the fluid outlet path. The outer cap assembly is slidable relative to the inner cap assembly between a first filling position, where the interior of the syringe is in fluid communication with the fluid inlet path, and a second delivery position, where the interior of the syringe is in fluid communication (Continued)

with the fluid outlet path. Syringes including the cap are also described.

16 Claims, 19 Drawing Sheets

(51) Int. Cl.
| | |
|---|---|
| *A61M 5/31* | (2006.01) |
| *A61M 5/315* | (2006.01) |
| *B65B 3/00* | (2006.01) |
| *B65B 7/28* | (2006.01) |
| *A61M 5/145* | (2006.01) |
| *A61M 39/24* | (2006.01) |

(52) U.S. Cl.
CPC ......... *A61M 5/31515* (2013.01); *B65B 3/003* (2013.01); *B65B 7/28* (2013.01); *A61M 2005/14553* (2013.01); *A61M 2005/3104* (2013.01); *A61M 2005/3114* (2013.01); *A61M 2039/2486* (2013.01); *A61M 2039/2493* (2013.01); *A61M 2205/3334* (2013.01); *A61M 2209/045* (2013.01)

(58) Field of Classification Search
CPC ........... A61M 2005/3114; A61M 2005/14553; A61M 5/31515; A61M 2039/224; A61M 5/1782; A61M 2039/2406; A61M 2039/2486; A61M 2039/2493; A61M 2209/045; B65B 3/003; B65B 7/28
See application file for complete search history.

(56) References Cited

U.S. PATENT DOCUMENTS

| | | | |
|---|---|---|---|
| 937,029 A | 10/1909 | Blessing et al. | |
| 1,930,929 A * | 10/1933 | Eisenberg | A61M 5/31 604/183 |
| 2,062,285 A * | 12/1936 | Bergman | A61M 1/63 417/466 |
| 2,514,575 A | 7/1950 | Hein et al. | |
| 2,592,381 A * | 4/1952 | Blackman | A61M 5/31511 604/222 |
| 2,667,163 A | 1/1954 | Smith | |
| 2,667,164 A | 1/1954 | Smith | |
| 2,667,165 A | 1/1954 | Smith | |
| 2,667,872 A | 2/1954 | Smith | |
| 2,672,866 A | 3/1954 | Kater | |
| 2,673,561 A | 3/1954 | Peterson, Jr. | |
| 2,688,963 A | 9/1954 | Smith | |
| 2,688,964 A | 9/1954 | Smith | |
| 2,690,179 A | 9/1954 | Fox | |
| 2,717,598 A | 9/1955 | Krasno | |
| 2,805,662 A | 9/1957 | Lawshe et al. | |
| 2,911,972 A | 11/1959 | Elinger | |
| 2,935,067 A | 5/1960 | Bouet | |
| 2,950,717 A | 8/1960 | Bonet | |
| 3,155,281 A | 11/1964 | Stracey | |
| 3,161,194 A | 12/1964 | Chapman | |
| 3,161,195 A | 12/1964 | Taylor et al. | |
| 3,172,577 A | 3/1965 | Hartung | |
| 3,190,619 A | 6/1965 | Penney et al. | |
| 3,231,139 A | 1/1966 | Bouet | |
| 3,301,293 A | 1/1967 | Santelli | |
| 3,340,869 A | 9/1967 | Bane | |
| 3,353,537 A * | 11/1967 | Knox | A61M 5/204 604/223 |
| 3,390,821 A | 7/1968 | Mullan | |
| 3,411,503 A | 11/1968 | Santomieri | |
| 3,442,424 A | 5/1969 | Sam et al. | |
| 3,471,058 A | 10/1969 | Peter et al. | |
| 3,473,524 A | 10/1969 | John | |
| 3,474,844 A | 10/1969 | Rudolph et al. | |
| 3,506,163 A | 4/1970 | James et al. | |
| 3,557,788 A | 1/1971 | Betty | |
| 3,613,963 A | 10/1971 | Otto | |
| 3,618,846 A | 11/1971 | Patrick | |
| 3,826,409 A | 7/1974 | Chilcoate | |
| 3,873,003 A | 3/1975 | Seiferth et al. | |
| 3,938,514 A | 2/1976 | Boucher | |
| 4,035,461 A | 7/1977 | Korth | |
| 4,044,836 A | 8/1977 | Martin et al. | |
| 4,064,879 A | 12/1977 | Leibinsohn | |
| 4,066,080 A | 1/1978 | Sneider | |
| 4,131,217 A | 12/1978 | Sandegren | |
| 4,136,802 A | 1/1979 | Mascia et al. | |
| 4,171,698 A | 10/1979 | Genese | |
| 4,349,129 A | 9/1982 | Amneus | |
| 4,392,491 A | 7/1983 | Takasugi et al. | |
| 4,411,656 A | 10/1983 | Cornett, III | |
| 4,526,296 A | 7/1985 | Berger et al. | |
| 4,753,638 A | 6/1988 | Peters | |
| 4,773,458 A | 9/1988 | Touzani | |
| 4,850,807 A | 7/1989 | Frantz | |
| 5,000,739 A | 3/1991 | Kulisz et al. | |
| 5,201,438 A | 4/1993 | Norwood | |
| 5,209,372 A | 5/1993 | Norwood | |
| 5,236,204 A | 8/1993 | Hempel | |
| 5,238,150 A | 8/1993 | Williams | |
| 5,240,130 A | 8/1993 | Osbakk | |
| 5,242,422 A | 9/1993 | Schneberger et al. | |
| 5,269,428 A | 12/1993 | Gilbert | |
| 5,333,761 A | 8/1994 | Davis et al. | |
| 5,353,961 A | 10/1994 | Debush | |
| 5,370,250 A | 12/1994 | Gilbert | |
| 5,383,858 A | 1/1995 | Reilly et al. | |
| 5,397,157 A | 3/1995 | Hempel et al. | |
| 5,573,129 A | 11/1996 | Nagata et al. | |
| 5,584,413 A | 12/1996 | Jung | |
| 5,592,948 A | 1/1997 | Gatten | |
| 5,609,580 A | 3/1997 | Kwiatkowski et al. | |
| 5,615,791 A | 4/1997 | Matelot et al. | |
| 5,638,995 A | 6/1997 | Mazda | |
| 5,683,369 A | 11/1997 | Tsukada | |
| 5,758,789 A | 6/1998 | Shin et al. | |
| 5,794,107 A | 8/1998 | Russell | |
| 5,827,233 A | 10/1998 | Futagawa et al. | |
| 5,836,922 A | 11/1998 | Hansen et al. | |
| 5,873,861 A | 2/1999 | Hitchins et al. | |
| 5,899,889 A | 5/1999 | Futagawa et al. | |
| RE36,377 E | 11/1999 | Gilbert | |
| 5,979,326 A | 11/1999 | Ohinata | |
| 6,054,194 A | 4/2000 | Kane | |
| 6,062,437 A | 5/2000 | Mascitelli | |
| 6,077,252 A | 6/2000 | Siegel | |
| 6,105,815 A | 8/2000 | Mazda | |
| 6,142,976 A | 11/2000 | Kubo | |
| 6,216,915 B1 | 4/2001 | Harman et al. | |
| 6,224,577 B1 | 5/2001 | Dedola et al. | |
| 6,250,505 B1 | 6/2001 | Petit | |
| 6,306,191 B1 | 10/2001 | McInerney et al. | |
| 6,315,761 B1 | 11/2001 | Shcherbina et al. | |
| 6,319,235 B1 | 11/2001 | Yoshino | |
| 6,332,876 B1 | 12/2001 | Poynter et al. | |
| 6,485,471 B1 | 11/2002 | Zivitz et al. | |
| 6,558,358 B2 | 5/2003 | Rosoff et al. | |
| 6,578,738 B1 | 6/2003 | Keller | |
| 6,620,134 B1 | 9/2003 | Trombley, III et al. | |
| 6,634,524 B1 | 10/2003 | Helmenstein | |
| 6,652,489 B2 | 11/2003 | Trocki et al. | |
| 6,702,143 B2 | 3/2004 | Wang | |
| 6,716,195 B2 | 4/2004 | Nolan, Jr. et al. | |
| 6,773,417 B2 | 8/2004 | Fitzgibbons et al. | |
| 6,840,164 B2 | 1/2005 | Eastman | |
| 6,866,039 B1 | 3/2005 | Wright et al. | |
| 6,869,419 B2 | 3/2005 | Dragan et al. | |
| RE38,770 E | 8/2005 | Gilbert | |
| 6,974,443 B2 | 12/2005 | Reilly et al. | |
| 7,004,213 B2 | 2/2006 | Hansen | |
| 7,011,650 B2 | 3/2006 | Rosoff et al. | |
| 7,192,549 B2 | 3/2007 | Hansen | |
| 7,250,039 B2 | 7/2007 | Fitzgerald | |

(56) References Cited

U.S. PATENT DOCUMENTS

| | | |
|---|---|---|
| 7,309,463 B2 | 12/2007 | Hansen |
| 7,513,378 B2 | 4/2009 | Mori et al. |
| 7,553,294 B2 | 6/2009 | Lazzaro et al. |
| 7,563,249 B2 | 7/2009 | Schriver et al. |
| 7,604,623 B2 | 10/2009 | Brunner et al. |
| 7,666,169 B2 | 2/2010 | Cowan et al. |
| 7,802,691 B2 | 9/2010 | Musalek et al. |
| 8,945,051 B2 | 2/2015 | Schriver et al. |
| 9,173,995 B1 | 11/2015 | Tucker et al. |
| 9,180,252 B2 | 11/2015 | Gelblum et al. |
| 9,199,033 B1 | 12/2015 | Cowan et al. |
| 9,474,857 B2 | 10/2016 | Riley et al. |
| 10,124,110 B2 | 11/2018 | Dedig et al. |
| 10,507,319 B2 | 12/2019 | Haury et al. |
| 10,583,256 B2 | 3/2020 | Berry et al. |
| 10,857,345 B2 | 12/2020 | Uber, III et al. |
| 10,933,190 B2 | 3/2021 | Berry et al. |
| 11,207,462 B2 | 12/2021 | Cowan et al. |
| 11,547,793 B2 | 1/2023 | Cowan et al. |
| 2004/0116893 A1 | 6/2004 | Spohn et al. |
| 2004/0249344 A1 | 12/2004 | Nemoto et al. |
| 2010/0091361 A1 | 4/2010 | Yuuki |
| 2010/0286650 A1* | 11/2010 | Fitzgerald ............ A61J 1/1412 604/249 |
| 2011/0009826 A1 | 1/2011 | Lewis |
| 2012/0020911 A1 | 1/2012 | Seliktar et al. |
| 2012/0253291 A1 | 10/2012 | Ivosevic et al. |
| 2013/0030291 A1 | 1/2013 | Lewis |
| 2013/0043273 A1* | 2/2013 | Lee .................... B05B 11/0083 222/129 |
| 2013/0204130 A1* | 8/2013 | McArthur ............ A61M 5/007 600/432 |
| 2013/0211248 A1 | 8/2013 | Cowan et al. |
| 2014/0124087 A1* | 5/2014 | Anderson ................ A61M 5/19 141/2 |
| 2016/0114100 A1* | 4/2016 | Cowan .............. A61M 5/14546 604/154 |
| 2016/0250409 A1* | 9/2016 | Dedig ................... A61M 5/007 600/432 |
| 2017/0028131 A1 | 2/2017 | Perazzo et al. |
| 2017/0035974 A1 | 2/2017 | Berry et al. |

FOREIGN PATENT DOCUMENTS

| | | | |
|---|---|---|---|
| EP | 2098258 A1 | 9/2009 | |
| EP | 2767299 A1 * | 8/2014 | ............ A61M 39/24 |
| FR | 1288915 A | 3/1962 | |
| GB | 2214819 A | 9/1989 | |
| GB | 2374143 A | 10/2002 | |
| WO | 9221391 A1 | 12/1992 | |
| WO | 2009038955 A1 | 3/2009 | |
| WO | 2010004206 A2 | 1/2010 | |
| WO | 2011129175 A1 | 10/2011 | |
| WO | 2012155035 A1 | 11/2012 | |
| WO | 2014027009 A1 | 2/2014 | |
| WO | 2015058088 A1 | 4/2015 | |
| WO | 2015066506 A2 | 5/2015 | |
| WO | 2015164783 A1 | 10/2015 | |
| WO | 2016058946 A1 | 4/2016 | |
| WO | 2016069711 A1 | 5/2016 | |
| WO | 2016069714 A1 | 5/2016 | |
| WO | 2016112163 A1 | 7/2016 | |
| WO | 2016157886 A1 | 10/2016 | |
| WO | 2016172467 A1 | 10/2016 | |
| WO | 2016191485 A1 | 12/2016 | |
| WO | 2017040154 A1 | 3/2017 | |
| WO | 2017091643 A1 | 6/2017 | |
| WO | 2017152036 A1 | 9/2017 | |
| WO | 2017184755 A1 | 10/2017 | |
| WO | 2018053074 A1 | 3/2018 | |
| WO | 2018075386 A1 | 4/2018 | |
| WO | 2019046259 A1 | 3/2019 | |
| WO | 2019046260 A1 | 3/2019 | |
| WO | 2019046267 A1 | 3/2019 | |
| WO | 2019046299 A1 | 3/2019 | |
| WO | 2019055497 A1 | 3/2019 | |
| WO | 2020055785 A1 | 3/2020 | |
| WO | 2020055818 A1 | 3/2020 | |

* cited by examiner

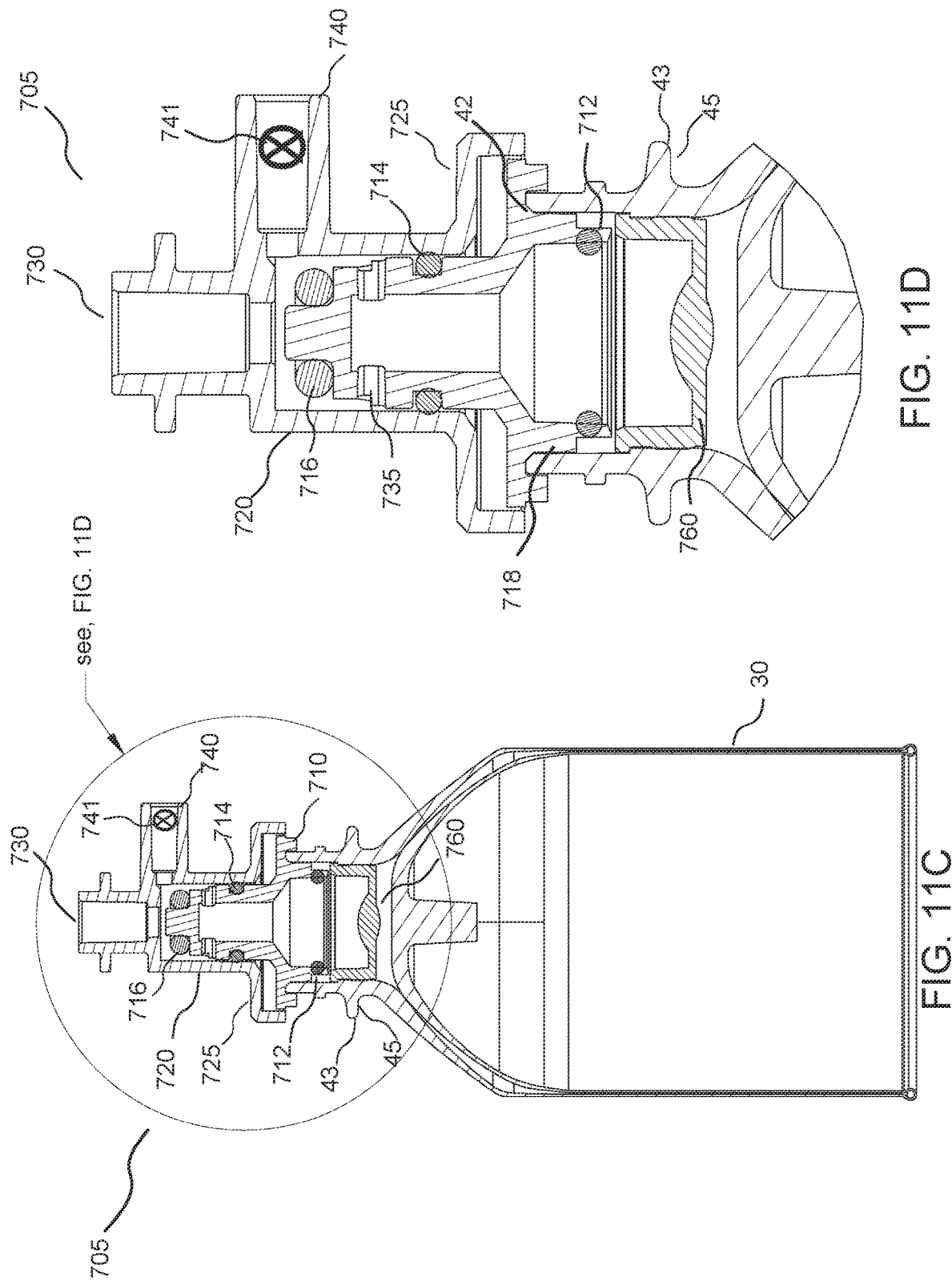

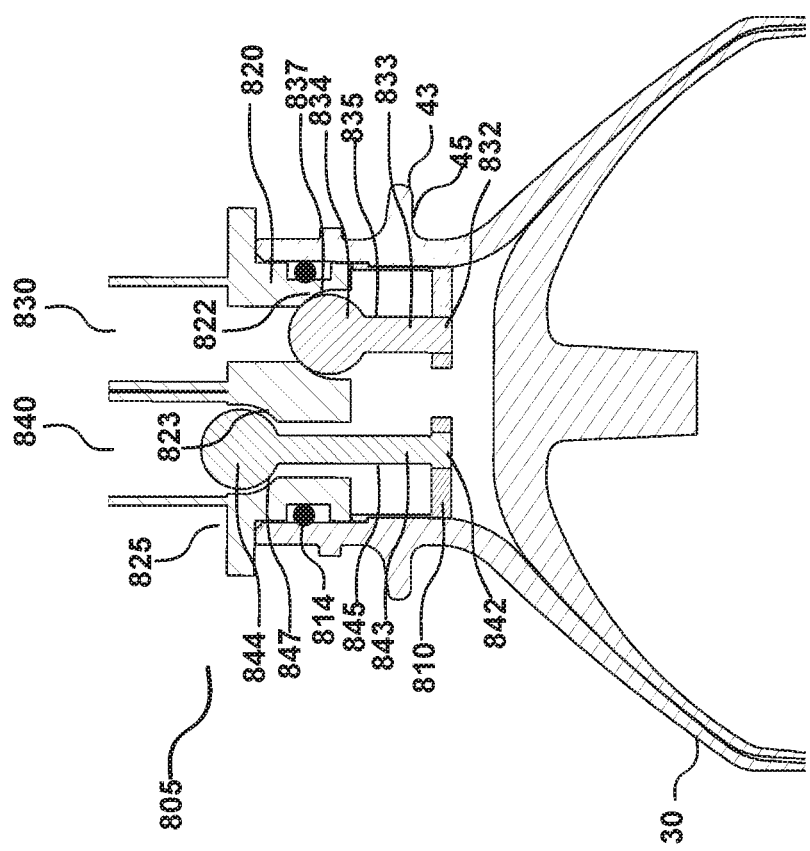
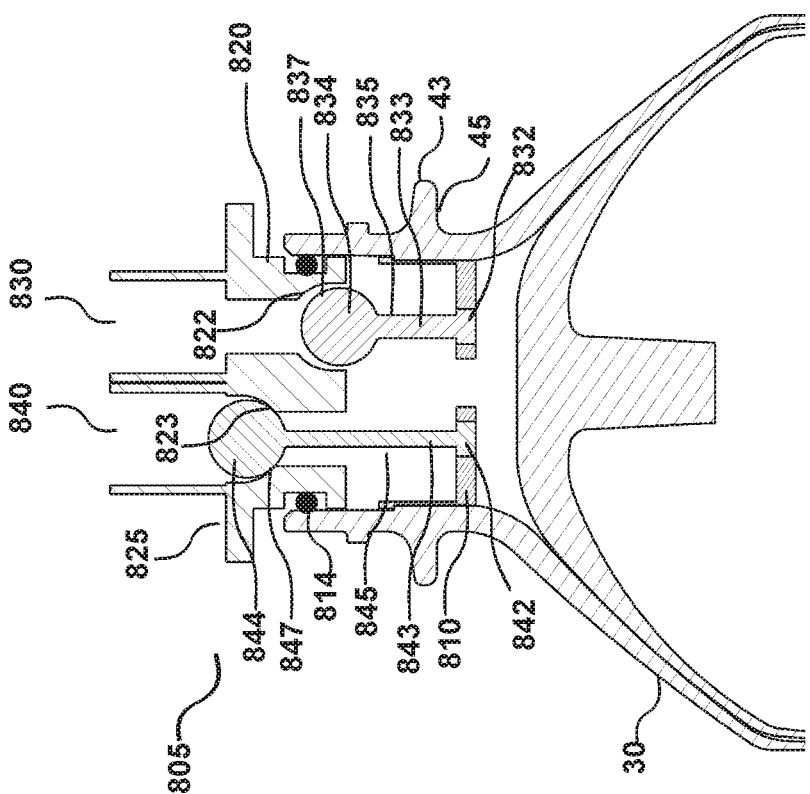

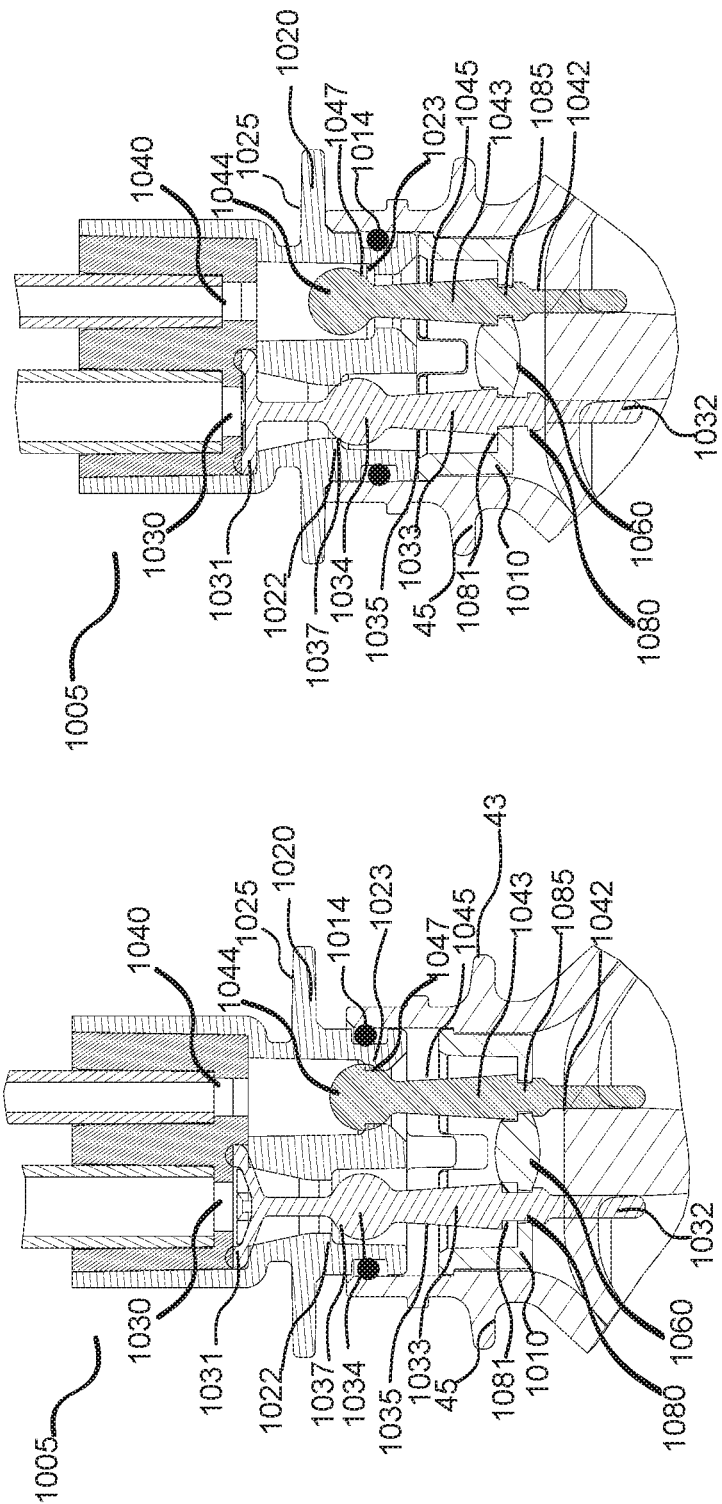

SLIDING SYRINGE CAP FOR SEPARATE FILLING AND DELIVERY

This application is a § U.S. national phase application under 35 U.S.C. § 371 of PCT International Application No. PCT/US2018/050640, filed 12 Sep. 2018 and claims priority to U.S. Provisional Application No. 62/558,012, titled "Sliding Syringe Cap for Separate Filling and Delivery," filed on 13 Sep. 2017, and U.S. Provisional Application No. 62/575,062, titled "Syringe Cap and Syringe Retaining Mechanism," filed on 20 Oct. 2017, the disclosures of which are incorporated herein in their entirety.

BACKGROUND OF THE DISCLOSURE

Field of the Technology

The present disclosure relates generally to syringes having a cap configured for use with fluid injectors having the one or more syringe retention features, wherein the cap includes a sliding feature for separate fluid filling and fluid delivery processes.

Description of Related Art

In many medical diagnostic and therapeutic procedures, a medical practitioner, such as a physician, injects a patient with one or more medical fluids. In recent years, a number of injector-actuated syringes and powered fluid injectors for pressurized injection of medical fluids, such as a contrast solution (often referred to simply as "contrast"), a flushing agent, such as saline, and other medical fluids, have been developed for use in procedures such as angiography, computed tomography (CT), ultrasound, magnetic resonance imaging (MRI), positron emission tomography (PET), and other imaging procedures. In general, these fluid injectors are designed to deliver a preset amount of fluid at a preset pressure and/or flow rate.

Typically, fluid injectors have at least one drive member, such as pistons, that connects to the syringe, for example via a connection with a plunger or an engagement feature on the syringe. The syringe generally includes a rigid barrel with the syringe plunger being slidably disposed within the barrel. In other embodiments, the syringe may include a rolling diaphragm barrel configuration having a flexible sidewall, where the proximal end of the syringe body releasably interacts with the at least one drive member. The drive members drive the plungers or the rolling diaphragm/proximal end in a proximal and/or distal direction relative to a longitudinal axis of the barrel to draw fluid into the syringe barrel or deliver the fluid from the syringe barrel.

Syringes for use with fluid injectors may be made of various medical-grade plastic materials with a certain minimum wall thickness. Syringe thickness is an important design factor, as fluid pressures of up to 1200 psi may be used during an injection procedure. During certain injection procedures, the syringe itself may not be capable of withstanding the high pressure without excessive radial expansion of the syringe wall under such pressure. This may result in undesired changes in fluid delivery volumes and flow rates. Fluid injectors having at least one pressure jacket have been developed for enclosing the syringe and preventing radial expansion of the syringe due to buildup of fluid pressure within the syringe. Conventional pressure jacket designs include a rigid cylindrical pressure jacket that engages a rigid cap at the distal end to maintain the syringe within the pressure jacket.

Conventional syringe design includes an integrated syringe inlet/outlet, such as a luer-tipped nozzle at the distal end of the syringe which may be connected to a fluid path for fluid filling and/or delivery processes. However, these systems typically require an operator to switch the fluid path connections between filling the syringe with a medical fluid and delivery of the medical fluid to the patient, leading to potential contamination issues, air intake, and/or requiring additional time for the medical procedure preparation.

SUMMARY OF DISCLOSURE

The present disclosure generally relates to caps for syringes that may switch or slide between a first, filling position where the syringe is in fluid communication with a bulk fluid container for filling the syringe and a second, delivery position where the syringe is in fluid communication with a fluid path for delivery of a fluid to a patient. In other embodiments, the syringe cap may slide to a third, closed position where the interior of the syringe is isolated from the filling and delivery fluid paths.

According to a first embodiment, a sliding cap for a syringe is described. The cap may comprise an outer cap assembly comprising a fluid inlet path and a fluid outlet path; and an inner cap assembly configured for insertion into a fluid nozzle of the syringe and to provide selective fluid communication between an interior of a syringe and the fluid inlet path or the fluid outlet path. According to various embodiments, the outer cap assembly is slidable relative to the inner cap assembly between a first filling position and a second delivery position. When the cap is in the first filling position, the interior of the syringe is in fluid communication with the fluid inlet path and when the cap is in the second delivery position, the interior of the syringe is in fluid communication with the fluid outlet path.

In other examples, the inner cap assembly may further comprise a flow diverter feature to divert flow of a fluid to the inner walls of the syringe when the syringe is being filled with the fluid. The flow diverter may allow for rapid and/or bubble free intake of liquid into the syringe by utilizing a Coandã effect (see WO 2017091643, the disclosure of which is incorporated herein by this reference).

In various embodiments, the outer cap assembly may have an engagement feature configured to engage a cap retention feature of a fluid injector, such as a distal surface that is substantially flat. The engagement feature prevents movement of the outer cap assembly in at least one of the proximal direction and the distal direction when the engagement feature is engaged with the cap retention feature of the fluid injector. According to various embodiments, when the engagement feature engages a surface of the cap retention feature of the fluid injector, the outer cap assembly is slidable relative to the inner cap assembly upon distal and proximal movement of the syringe having the cap attached thereto. In certain embodiments, the outer cap assembly slides relative to the inner cap assembly into the first filling position when one of a plunger of the syringe and a proximal end wall of the syringe is drawn in a proximal direction by a piston or drive member of the fluid injector. In certain embodiments, the outer cap assembly slides relative to the inner cap assembly into the second delivery position when one of a plunger of the syringe and a proximal end wall of the syringe is moved in a distal direction by a piston or drive member of the fluid injector. According to various embodiments, the cap slides between the first filling position and the second delivery position when the direction of movement of the plunger or the proximal end wall of the syringe is changed from the proximal direction to the distal direction, and vice versa. According to various embodiments, the fluid nozzle is located at a distal discharge neck of the syringe.

According to certain embodiments, at least one of the fluid inlet path and the fluid outlet path includes a closure member configured to move between a closed position and an open position upon sliding of the outer cap assembly relative to the inner cap assembly. For example, the closure member may slide from the open position to the closed position upon sliding of the outer cap assembly relative to the inner cap assembly in one of the distal and proximal direction and may slide from the closed position to the open position upon sliding of the outer cap assembly relative to the inner cap assembly in other of the distal and proximal direction. According to certain embodiments, the closure member comprises a first portion having a sealing surface for creating a fluid tight seal with a surface associated with the at least one of the fluid inlet path and the fluid outlet path, when the closure member is in the closed position. The closure member further comprises a second portion and an elastic connector member between the first portion and the second portion, wherein the elastic connector member connects the closure member to the inner cap assembly and wherein the elastic connector member is configured to at least one of stretch, compress, or bend as the closure member moves between the open position and the closed position. For example according to certain embodiments, the elastic connector member comprises a plurality of bendable legs connecting the elastic connector member to the inner cap assembly, and wherein the plurality of bendable legs bend as the closure member moves between the open position and the closed position. In other embodiments, the elastic connector member is attached to the inner cap assembly at the second end and stretches or compresses as the closure member moves between the open position and the closed position. In various embodiments, the fluid inlet path comprises an inlet closure member and the fluid outlet path comprises an outlet closure member, wherein the inlet closure member is in an open position when the syringe is being filled with a liquid and in a closed position when the syringe is delivering the liquid, and wherein the outlet closure member is in a closed position when the syringe is being filled with a liquid and in an open position when the syringe is delivering the liquid.

In other embodiments, the outer cap assembly may be slidable relative to the inner cap assembly to a third closed position where there is no fluid communication between the interior of the syringe and the fluid inlet path or the fluid outlet path. When the cap is in the closed position, no fluid flow between the interior of the syringe and the fluid inlet path or the fluid outlet path occurs. For example, when the syringe is under vacuum or when the syringe is pressurized by moving the piston in the proximal direction or the distal direction, respectively, the cap may slide into the third closed position where the interior of the syringe is fluidly isolated from the fluid inlet path and the fluid outlet path.

In various examples, the cap may be configured to fit within a distal discharge neck of a syringe. The fit between the cap and the syringe may be fluid tight so that no fluid leakage occurs at the connection between the cap and the fluid nozzle of the syringe. In various examples, the inner cap assembly may comprise one or more O-rings or other sealing features to provide the fluid tight seal.

According to various embodiments, the syringe may be a front loading syringe or a rolling diaphragm syringe.

Other embodiments of the present disclosure are directed to a syringe for use with a fluid injector. According to these embodiments, the syringe may comprise a proximal end, a distal end, and a cylindrical sidewall between the proximal end and the distal end defining an interior volume for retaining a medical fluid therein; a discharge nozzle at the distal end; a piston engagement feature located on one of plunger slidably associated with the syringe and a proximal end wall of the syringe, the piston engagement feature configured for releasably engaging a piston of the fluid injector; and a cap at least partially inserted into or otherwise engaged with the discharge nozzle and configured to take fluid in and deliver a fluid from the syringe. According to various embodiments, the cap may include any embodiment of the syringe caps described herein. In specific embodiments, the syringe may be configured to fit into a pressure jacket associated with a fluid injector. The syringe may further comprise a retention feature or retention flange having a proximal surface that engages a feature of the fluid injector and limits a distance that the syringe may slide in the proximal direction when the plunger or the end wall is retracted in the proximal direction. In specific embodiments, the syringe may be a rolling diaphragm syringe. In other embodiments, the syringe may be a front loading syringe for a medical fluid injector.

Various aspects of the system and method for injector position calibration of the fluid injector are disclosed in one or more of the following numbered clauses:

Clause 1. A cap for intake and delivery of a fluid from a syringe, the cap comprising: an outer cap assembly comprising a fluid inlet path and a fluid outlet path; and an inner cap assembly configured for insertion into a fluid nozzle of the syringe and to provide selective fluid communication between an interior of a syringe and the fluid inlet path or the fluid outlet path, wherein the outer cap assembly is slidable relative to the inner cap assembly between a first filling position, where the interior of the syringe is in fluid communication with the fluid inlet path, and a second delivery position, where the interior of the syringe is in fluid communication with the fluid outlet path.

Clause 2. The cap of clause 1, wherein the inner cap assembly further comprises a flow controller feature to divert flow of a fluid to the inner walls of the syringe when the syringe is being filled with the fluid.

Clause 3. The cap of clause 1 or 2, wherein the outer cap assembly has an engagement feature configured to engage a cap retention feature of a fluid injector, wherein the engagement surface prevents movement of the outer cap assembly in at least one of the proximal direction and the distal direction when the engagement feature is engaged with the cap retention feature.

Clause 4. The cap of clause 3, wherein when the engagement feature engages a surface of the cap retention feature of the fluid injector, the outer cap assembly is slidable relative to the inner cap assembly upon distal and proximal movement of the syringe having the cap attached thereto.

Clause 5. The cap of any one of claims 1 to 4, wherein the cap is in the first filling position when one of a plunger and a proximal end wall of the syringe is drawn in a proximal direction by a piston of the fluid injector.

Clause 6. The cap of any one of clauses 1 to 5, wherein the cap is in the second delivery position when one of a plunger and a proximal end wall of the syringe is pushed in a distal direction by a piston of the fluid injector.

Clause 7. The cap of any one of clauses 1 to 6, wherein the cap slides between the first filling position and the second delivery position when the direction of movement of the plunger or the proximal end wall of the syringe is changed from the proximal direction to the distal direction.

Clause 8. The cap of any one of clauses 1 to 7, wherein the fluid nozzle is located at a distal discharge neck of the syringe.

Clause 9. The cap of any one of clauses 1 to 8, wherein at least one of the fluid inlet path and the fluid outlet path includes a closure member configured to move between a closed position and an open position upon sliding of the outer cap assembly relative to the inner cap assembly.

Clause 10. The cap of clause 9, wherein the closure member comprises: a first portion having a sealing surface for creating a fluid tight seal with a surface associated with the at least one of the fluid inlet path and the fluid outlet path when the closure member is in the closed position; a second portion; and an elastic connector member between the first portion and the second portion, wherein elastic connector member connects the closure member to the inner cap assembly, wherein the elastic connector member is configured to at least one of stretch, compress, or bend as the closure member moves between the open position and the closed position.

Clause 11. The cap of clause 10, wherein the elastic connector member comprises a plurality of bendable legs connecting the elastic connector member to the inner cap assembly, and wherein the plurality of bendable legs bend as the closure member moves between the open position and the closed position.

Clause 12. The cap of clause 10, wherein the elastic connector member stretches or compresses as the closure member moves between the open position and the closed position.

Clause 13. The cap of any of clauses 1 to 12, wherein the fluid inlet path comprises an inlet closure member and the fluid outlet path comprises an outlet closure member, wherein the inlet closure member is in an open position when the syringe is being filled with a liquid and in a closed position when the syringe is delivering the liquid, and wherein the outlet closure member is in a closed position when the syringe is being filled with a liquid and in an open position when the syringe is delivering the liquid.

Clause 14. The cap of any one of clauses 1 to 13, wherein the outer cap assembly is slidable relative to the inner cap assembly to a third closed position where there is no fluid communication between the interior of the syringe and the fluid inlet path or the fluid outlet path.

Clause 15. The cap of any one of clauses 1 to 14, wherein the syringe is one of a front loading syringe, and a rolling diaphragm syringe.

Clause 16. A syringe for a fluid injector, the syringe comprising: a proximal end, a distal end, and a cylindrical sidewall between the proximal end and the distal end defining an interior volume for retaining a medical fluid therein; a discharge nozzle at the distal end; a piston engagement feature located on one of plunger slidably associated with the syringe and a proximal end wall of the syringe, the piston engagement feature configured for releasably engaging a piston of the fluid injector; and a cap at least partially inserted into the discharge nozzle and configured to intake and deliver of a fluid from the syringe, the cap comprising: an outer cap assembly comprising a fluid inlet path and a fluid outlet path; and an inner cap assembly configured for insertion into a fluid nozzle of the syringe and to provide selective fluid communication between an interior of a syringe and the fluid inlet path or the fluid outlet path, wherein the outer cap assembly is slidable relative to the inner cap assembly between a first filling position, where the interior of the syringe is in fluid communication with the fluid inlet path, and a second delivery position, where the interior of the syringe is in fluid communication with the fluid outlet path.

Clause 17. The syringe of clause 16, wherein the syringe is configured to fit into a pressure jacket associated with the fluid injector.

Clause 18. The syringe of clause 16 or 17, the syringe further comprising a retention flange having a proximal surface that limits a distance that the syringe slides in a proximal direction when the plunger or the end wall is retracted in the proximal direction.

Clause 19. The syringe of any one of clauses 16 to 18, wherein the outer cap assembly has an engagement feature configured to engage a cap retention feature of a fluid injector, wherein the engagement surface prevents movement of the outer cap assembly in at least one of the proximal direction and the distal direction when the engagement feature is engaged with the cap retention feature.

Clause 20. The syringe of clause 19, wherein when the engagement feature engages a surface of the cap retention feature, the outer cap assembly is slidable relative to the inner cap assembly upon distal and proximal movement of the syringe having the cap attached thereto.

Clause 21. The syringe of any one of clauses 16 to 20, wherein the cap is in the first filling position when one of the plunger and the proximal end wall of the syringe is drawn in a proximal direction by the piston of the fluid injector.

Clause 22. The syringe of any one of clauses 16 to 21, wherein the cap is in the second delivery position when one of a plunger and a proximal end wall of the syringe is pushed in a distal direction by a piston of the fluid injector.

Clause 23. The syringe of any one of clauses 16 to 22, wherein the cap slides between the first filling position and the second delivery position when the direction of movement of the plunger or the proximal end wall of the syringe is changed from the proximal direction to the distal direction.

Clause 24. The syringe of any one of clauses 16 to 23, wherein at least one of the fluid inlet path and the fluid outlet path includes a closure member configured to move between a closed position and an open position upon sliding of the outer cap assembly relative to the inner cap assembly.

Clause 25. The syringe of any of clauses 16 to 24, wherein the fluid inlet path comprises an inlet closure member and the fluid outlet path comprises an outlet closure member, wherein the inlet closure member is in an open position when the syringe is being filled with a liquid and in a closed position when the syringe is delivering the liquid, and wherein the outlet closure member is in a closed position when the syringe is being filled with a liquid and in an open position when the syringe is delivering the liquid.

Clause 26. The syringe of any one of clauses 16 to 25, wherein the outer cap assembly is slidable relative to the inner cap assembly to a third closed position where there is no fluid communication between the interior of the syringe and the fluid inlet path or the fluid outlet path.

Clause 27. The syringe of any one of clauses 1 to 14, wherein the syringe is a rolling diaphragm syringe.

Further details and advantages of the various aspects described in detail herein will become clear upon reviewing the following detailed description of the various aspects in conjunction with the accompanying drawing figures.

BRIEF DESCRIPTION OF THE DRAWINGS

FIGS. 11A to 11F illustrate a top perspective view of sliding syringe cap FIG. 11A according to an embodiment including an exploded view FIG. 11B. The syringe cap is shown in the filling position FIG. 11C, including a detail illustration of the sliding cap FIG. 11D; and in a delivery position FIG. 11E, including a detail illustration of the sliding cap FIG. 11F;

FIGS. 12A to 12C illustrate an embodiment of the syringe cap including a fluid inlet closure member and an outlet closure member in the fill position FIG. 12A, the delivery position FIG. 12B, and in the closed position FIG. 12C;

FIGS. 14A to 14C illustrate an embodiment of the syringe cap including a fluid inlet closure member and an outlet closure member in the fill position FIG. 14A, the delivery position FIG. 14B, and in the closed position FIG. 14C.

DETAILED DESCRIPTION

Figure 1:
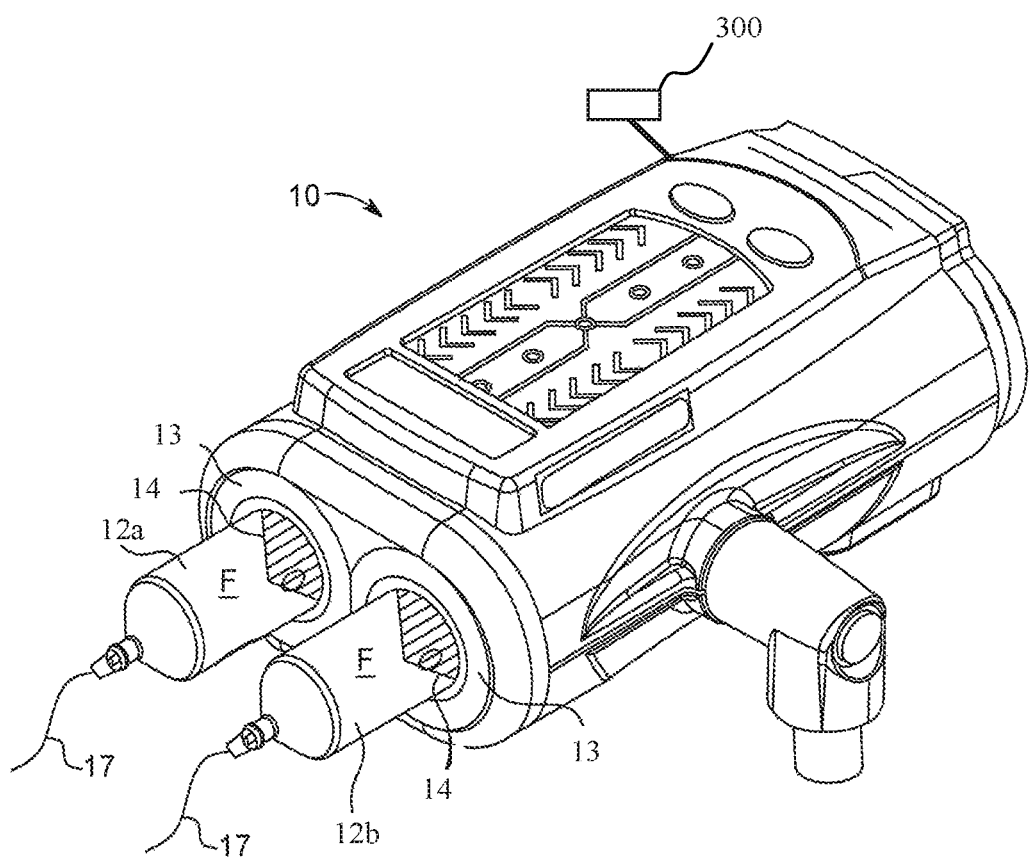
FIG. 1 is a perspective view of a fluid delivery system for use with a syringe and syringe cap according to an example of the present disclosure.

As used in the specification, the singular form of "a", "an", and "the" include plural referents unless the context clearly dictates otherwise.

For purposes of the description hereinafter, the terms "upper", "lower", "right", "left", "vertical", "horizontal", "top", "bottom", "lateral", "longitudinal", and derivatives thereof shall relate to the components as they are oriented in the drawing figures. When used in relation to a syringe and/or a pressure jacket, the term "proximal" refers to a portion of a syringe and/or a pressure jacket nearest to an injector when a syringe and/or a pressure jacket is oriented for connecting to an injector. The term "distal" refers to a portion of a syringe and/or a pressure jacket farthest away from an injector when a syringe and/or a pressure jacket is oriented for connecting to an injector. The term "radial" refers to a direction in a cross-sectional plane normal to a longitudinal axis of a syringe and/or a pressure jacket extending between proximal and distal ends. The term "circumferential" refers to a direction around an inner or outer surface of a sidewall of a syringe and/or a pressure jacket. The term "axial" refers to a direction along a longitudinal axis of a syringe and/or a pressure jacket extending between the proximal and distal ends. The term "flexible", when used in connection with a syringe, means that at least a portion of a syringe, such as a sidewall of a syringe, is capable of bending or being bent to change a direction in which it extends. The terms "roll over", "rolling over", and "rolls upon itself" refer to an ability of a first portion of a syringe, such as a proximal portion of a sidewall of a syringe, to bend approximately 180° relative to a second portion of a syringe, such as a distal portion of a sidewall of a syringe, when urged by a piston of a fluid injector. The term "closed" when used to refer to a fluid delivery component means that the system is not in fluid connection with an outlet, for example where fluid flow is stopped by the cap, a closure member, or a valve, such as a stopcock, high crack pressure valve, pinch valve, and the like.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

It is to be understood that the specific devices and processes illustrated in the attached drawings, and described in the following specification, are simply exemplary aspects of the disclosure. Hence, specific dimensions and other physical characteristics related to the aspects disclosed herein are not to be considered as limiting.

All documents, such as but not limited to issued patents and patent applications, referred to herein, and unless otherwise indicated, are to be considered to be "incorporated by reference" in their entirety.

Referring to the drawings in which like reference characters refer to like parts throughout the several views thereof, the present disclosure is generally directed to caps for syringes that may switch or slide between a first, filling position where the syringe is in fluid communication with a bulk fluid container for filling the syringe and a second, delivery position where the syringe is in fluid communication with a fluid path for delivery of a fluid to a patient. In other embodiments, the syringe cap may slide to a third, closed position where the interior of the syringe is isolated from the filling and delivery fluid paths.

According to a first embodiment, a sliding cap for a syringe is described. The cap may comprise an outer cap assembly comprising a fluid inlet path and a fluid outlet path and an inner cap assembly. The inner cap assembly may be configured for insertion into or may be otherwise engageable with a fluid nozzle of the syringe, such as by attaching to, adhering, or clipping onto,. The cap provides selective fluid communication between an interior of a syringe and the fluid inlet path or the fluid outlet path. That is, in a first configuration the cap provides fluid communication between the fluid inlet path and the interior of the syringe while preventing fluid communication between the fluid outlet path and the interior of the syringe, whereas in a second configuration the cap provides fluid communication between the fluid outlet path and the interior of the syringe while preventing fluid communication between the fluid inlet path and the interior of the syringe. According to various embodiments, the outer cap assembly may be slidable relative to the inner cap assembly between a first filling position and a second delivery position. For example, the outer cap assembly may slide relative to the inner cap assembly that is engaged with the fluid nozzle of the syringe as a syringe is moved in a proximal direction or a distal direction during a fluid intake or delivery procedure. When the cap is in the first filling position, the interior of the syringe is in fluid communication with the fluid inlet path while the fluid outlet path is not in fluid communication with the interior of the syringe and when the cap is in the second delivery position, the interior of the syringe is in fluid communication with the fluid outlet path while the fluid inlet path is not in fluid communication with the interior of the syringe.

In other examples, the inner cap assembly may further comprise a flow diverter feature to divert flow of a fluid to the inner walls of the syringe when the syringe is being filled with the fluid. According to these embodiments flow diverter may allow for rapid and/or bubble free intake of liquid into the syringe by utilizing a Coandã effect (see WO 2017/091643, the disclosure of which is incorporated herein by this reference). For example, by diverting the liquid to the flow down the inner walls of the syringe, the fluid may adhere to the inner walls of the syringe and have a more laminar-type flow during the filling process while reducing the tumbling and mixing of the fluid with air, allowing for a faster fill rate. Further, by diverting the liquid to the flow down the inner walls of the syringe, splashing of the fluid in the interior of the syringe and the corresponding production of bubbles in the syringe is avoided.

In various embodiments, the outer cap assembly may have an engagement feature configured to engage a cap retention feature of a fluid injector, such as a distal surface that is substantially flat or a flange around an outer circumference of the outer cap assembly, or other surface that engages the cap retention feature. The engagement feature prevents axial movement of the outer cap assembly in at least one of the proximal direction and the distal direction when the engagement feature is engaged with the cap retention feature of the fluid injector. The engagement feature may still allow the inner cap assembly to slide relative to the outer cap assembly as the syringe is moved in the distal and/or proximal direction. As used herein, when the outer cap assembly slides relative to the inner cap assembly includes where the outer cap assembly remains axially fixed and the inner cap assembly slides proximally and/or distally, the inner cap assembly remains axially fixed and the outer cap assembly slides proximally and/or distally, or both the outer cap assembly and the inner cap assembly slide in opposite directions or may slide in the same direction but at different rates. In certain embodiments, the engagement feature may prevent axial movement of the outer cap assembly in the distal direction when the engagement feature is engaged with the cap retention feature of the fluid injector. In certain embodiments, the engagement feature may prevent axial movement of the outer cap assembly in the proximal direction when the engagement feature is engaged with the cap retention feature of the fluid injector. According to other embodiments, the syringe and the inner cap assembly may be axially fixed and the outer cap may move distally and/or proximally, for example by movement of a retention mechanism of the injector that is engaged with the outer cap assembly. Examples of an engagement feature may include a pressure jacket cap releasably engageable with a distal end of a pressure jacket; or a surface or flange that engages or abuts a cap retention surface feature or retention slot of the fluid injector. Other suitable examples of cap retention features are described in U.S. Provisional Application No. 62/729,642, entitled "Injector Syringe Interface," filed on 11 Sep. 2018, the disclosure of which is incorporated in its entirety. According to various embodiments, when the engagement feature engages a surface of the cap retention feature of the fluid injector, the outer cap assembly is slidable relative to the inner cap assembly upon distal and proximal movement of the syringe having the cap attached thereto. In certain embodiments, the cap slides into the first filling position when one of a plunger of the syringe and a proximal end wall of the syringe is drawn in a proximal direction by a piston or drive member of the fluid injector. In certain embodiments, the cap slides into the second delivery position when one of a plunger of the syringe and a proximal end wall of the syringe is moved in a distal direction by a piston or drive member of the fluid injector. According to various embodiments, the cap slides from the first filling position to the second delivery position when the direction of movement of the plunger or the proximal end wall of the syringe is changed from the proximal direction to the distal direction, and the cap slides from the second delivery position to the first filling position when the direction of movement of the plunger or the proximal end wall of the syringe is changed from the distal direction to the proximal direction.

According to various embodiments, the fluid nozzle is located at distal end of the syringe, for example at a distal discharge neck of the syringe. In certain embodiments, the fluid nozzle may be configured and size so that the inner cap assembly may at least partially be inserted into and create a fluid tight fit between an outer surface of the inner cap assembly and an inner surface of the fluid nozzle. For example, one or both of the outer surface of the inner cap assembly and the inner surface of the fluid nozzle may comprise one or more sealing features, such as one or more O-rings, to create the fluid tight seal therebetween. In other embodiments, the inner cap assembly may be glued or otherwise adhered to the fluid nozzle. In other embodiments, the inner cap assembly may include one or more retention features, such as one or more clips to secure the inner cap assembly and the fluid nozzle. In certain embodiments, at least a portion of the inner cap assembly may fit around and be adhered to an outer surface of the fluid nozzle to create the fluid tight seal.

In embodiments of the present disclosure, the outer cap assembly and the inner cap assembly are slidable relative to one another, as described herein. According to certain embodiments, the inner and outer cap assemblies are slidable relative to each other due to the interface between an outer surface of the inner cap assembly and an inner surface of the outer cap assembly. One of skill in the art will also recognize, based on the present disclosure, that embodiments, where the inner and outer cap assemblies are slidable relative to each other due to the interface between an inner surface of the inner cap assembly and an outer surface of the outer cap assembly. According to the various embodiments, the slidable interface between the inner cap assembly and the outer cap assembly may be fluid tight, for example to prevent fluid leakage between the open position and the closed position during an injection or filling procedure. The fluid tight seal at the interface may be due to one or more sealing surfaces associated with at least one of the inner cap assembly and the outer cap assembly, for example one or more O-rings around an outer or inner surface of or groove in the inner cap assembly and/or one or more O-rings around an inner or outer surface of or groove in the outer cap assembly. In other embodiments, a fluid tight seal may result from a sealing surface molded into a surface of the at least one of the inner cap assembly and the outer cap assembly, for example an elastomeric flange such as by a 2-shot molding process, or a rolling diaphragm member attaching the outer cap assembly and/or the inner cap assembly to the inner wall of the fluid nozzle. The cap may further comprise one or more O-rings or elastomeric surfaces located on one or more of the out cap assembly and the inner cap assembly for fluidly sealing at least one of the first inlet path and the fluid outlet path According to certain embodiments, at least one of the fluid inlet path and the fluid outlet path may include a closure member configured to move between a closed position and an open position upon sliding of the outer cap assembly relative to the inner cap assembly to allow or prevent fluid flow therethrough. For example, the closure member may slide from the open position to the closed position upon sliding of the outer cap assembly relative to the inner cap assembly in one of the distal direction and proximal direction and may slide from the closed position to the open position upon sliding of the outer cap assembly relative to the inner cap assembly in other of the distal and proximal direction.

According to certain embodiments, the closure member may comprise a first portion having a sealing surface for creating a fluid tight seal with a surface associated with the at least one of the fluid inlet path and the fluid outlet path, when the closure member is in the closed position. For example, the sealing surface of the first portion may be hemispherical, conical, arced, or flat and may be formed from an elastomeric polymeric material that may form a sealing interface with a corresponding hemispherical or conical surface associated with the fluid inlet path or the fluid outlet path. In other embodiments, the surface associated with the fluid inlet path or outlet path may also have an elastomeric sealing surface. In still other embodiments, the surface of the closure member may be rigid and the surface associated with the fluid inlet path and/or the fluid outlet path may be elastomeric to provide a sealing interaction. Other shapes for the first portion and corresponding sealing surface are contemplated and within the scope of the present disclosure. As the sealing surface of the first portion and the corresponding surface associated with the at least one of the fluid inlet path and the fluid outlet path come into contact, for example in response to the distally or proximally sliding of the outer cap assembly relative to the inner cap assembly, a fluid tight seal is formed therebetween, blocking fluid communication past the seal. As the sealing surface of the first portion and the corresponding surface associated with the at least one of the fluid inlet path and the fluid outlet path disengage, the fluid tight seal is broken and fluid communication across the interface is achieved.

The closure member may further comprise a second portion and an elastic connector member between the first portion and the second portion. According to certain embodiments the elastic connector member may connect the closure member to the inner cap assembly. The elastic connector member may be formed from an elastomeric polymer or spring and may be configured to stretch, compress, and/or bend as the closure member moves between the open position and the closed position in response to sliding of the outer cap assembly relative to the inner cap assembly.

As the elastic connector member stretches, compresses, and/or bends, the sealing surface of the first portion is contacted with or disengaged from the corresponding surface associated with the at least one of the fluid inlet path and the fluid outlet path, thereby forming or breaking a fluid tight seal therebetween.

According to certain embodiments, the elastic connector member may comprise a plurality of bendable legs extending from the second portion of the elastic connector member and connecting to or abutting a surface of the outer cap assembly, and wherein the plurality of bendable legs bend as the closure member moves between the open position and the closed position. According to certain embodiments, the bendable legs comprise a first leg end connected to the second portion, a second leg end connected to or abutting the surface of the outer cap assembly, and a bendable portion between the first leg end and the second leg end that bends in response to the sliding of the outer cap assembly relative to the inner cap assembly. The bending of the plurality of bendable legs results in the formation or breaking of the seal between the sealing surface of the first portion and the corresponding surface of the outer cap assembly.

In other embodiments, the elastic connector member may be attached to the inner cap assembly at the second portion and may stretch or compress as the closure member moves between the open position and the closed position, thereby breaking or creating the fluid tight seal between the sealing surface of the first portion and the corresponding surface of the outer cap assembly. According to certain embodiments, an elastic connector member may stretch to form the fluid tight seal in the fluid outlet path, for example when the syringe is retracted in the proximal direction, thereby sliding the outer assembly cap distally relative to the inner cap assembly, during a filling operation. According to certain embodiments, an elastic connector member may compress to form the fluid tight seal in the fluid inlet path, for example when the syringe is moved in the distal direction, thereby sliding the outer assembly cap proximally relative to the inner cap assembly, during a delivery operation.

In various embodiments, the fluid inlet path comprises an inlet closure member and the fluid outlet path comprises an outlet closure member, wherein the inlet closure member is in an open position when the syringe is being filled with a liquid and in a closed position when the syringe is delivering the liquid, and wherein the outlet closure member is in a closed position when the syringe is being filled with a liquid and in an open position when the syringe is delivering the liquid. The inlet closure member and the outlet closure member may each be according to the embodiments of the closure members described herein. The inlet closure member and the outlet closure member may operate opposite of one another, for example, when the inlet closure member is in the open position, the outlet closure member may be in the closed position and when the inlet closure member is in the closed position, the outlet closure member may be in the open position. According to this configuration, the syringe may be selectively filled or used for delivery of fluid in a fashion that during the filling operation through the inlet fluid path, the outlet fluid path is in the closed position and during the delivery operation through the outlet fluid path, the inlet fluid path is in the closed position.

In other embodiments, the outer cap assembly may be slidable relative to the inner cap assembly to a third closed position where there is no fluid communication between the interior of the syringe and either of the fluid inlet path or the fluid outlet path. According to these embodiments, when the sliding syringe cap is in the third closed positions, there is also no fluid communication between the interior of the syringe and the interior of any other syringe associated with the injector. When the cap is in the third closed position, no fluid flow between the interior of the syringe and the fluid inlet path or the fluid outlet path occurs. For example, when the syringe is under vacuum or when the syringe is pressurized by moving the piston in the proximal direction or the distal direction, respectively, the cap may slide into the third closed position where the interior of the syringe is fluidly isolated from the fluid inlet path and the fluid outlet path. A system where both of the fluid inlet path and the fluid outlet path are closed to fluid communication with the interior of the syringe may have certain advantages, such as by limiting the effects on fluid flow due to syringe capacitance, such as swelling of the syringe volume when the contents are placed under pressure, particularly during phase transitions between a higher viscosity medical fluid, such as an imaging contrast medium, to a lower viscosity medical fluid, such as saline. Further, the third closed position may limit backflow of from a first syringe into the second syringe during fluid transitions. Such advantages are described in detail in the following International PCT Applications: PCT/US2017/020637; PCT/US2018/048282; PCT/US2018/048283; PCT/US2018/048294; and PCT/US2018/048338, the disclosures of each of which are incorporated herein by reference.

According to various embodiments, the third closed position may be slidably located in-between the first filling position and the second delivery position. In other embodiments, the third closed position may be slidably located proximal the first filling position. In another embodiment, third closed position may be slidably located distal to the second delivery position. According to other embodiments, the third closed position may be reached by slidably rotating the outer cap assembly relative to the inner cap assembly in one of the clockwise or counterclockwise direction. In this embodiment, the third closed position may be exited by slidably rotating the outer cap assembly relative to the inner cap assembly in the opposite counterclockwise or clockwise direction.

According to various embodiments, the sliding cap may have a spring biasing member between the outer cap assembly and the inner cap assembly to bias the sliding of the outer cap assembly relative to the inner cap assembly. For example, in one embodiment, the spring biasing member may bias the outer cap assembly and the inner cap assembly into the third closed position. According to this example, the cap may be biased to the third closed position when the piston is not moving in either the proximal or distal direction. In other embodiments, the spring biasing member may bias the cap into the fluid delivery position and in still other embodiments, the spring biasing member may bias the cap into the fluid filling position.

In various examples, the cap may be configured to at least partially fit within a fluid nozzle at a distal discharge neck of a syringe. For example, in certain embodiments, the inner cap assembly may be at least partially inserted into the fluid nozzle. The fit between the cap and the syringe may be fluid tight so that no fluid leakage occurs at the connection between the cap and the fluid nozzle of the syringe. In various examples, the inner cap assembly and/or outer cap assembly may comprise one or more O-rings or other sealing features to provide the fluid tight seal, as described herein. According to these embodiments, the inner cap assembly may be removably inserted into the fluid nozzle or may be permanently inserted into the fluid nozzle, for example by a friction fit or an adhesive.

According to various embodiments, the syringe may be a front loading syringe or a rolling diaphragm syringe, non-limiting examples of which are described herein.

Other embodiments of the present disclosure are directed to a syringe for use with a fluid injector. According to these embodiments, the syringe may comprise a proximal end, a distal end, and a cylindrical sidewall between the proximal end and the distal end defining an interior volume for retaining a medical fluid therein; a discharge nozzle at the distal end; a piston engagement feature located on one of plunger slidably associated with the syringe and a proximal end wall of the syringe, where the piston engagement feature may be configured for releasable engagement with a piston of the fluid injector; and a cap at least partially inserted into or otherwise engaged with the discharge nozzle and configured to take fluid in and deliver a fluid from the syringe. According to various embodiments, the cap may include any embodiment of the syringe caps described herein. In specific embodiments, the syringe may be configured to fit into a pressure jacket associated with a fluid injector. The syringe may further comprise at least one retention feature or retention flange having a proximal surface that engages at least one feature of the fluid injector and limits a distance that the syringe, and corresponding inner cap assembly may slide in the proximal direction when the plunger or the end wall is retracted in the proximal direction, with the outer cap assembly remaining substantially in the same lateral position. In specific embodiments, the syringe may be a rolling diaphragm syringe. In other embodiments, the syringe may be a front loading syringe for a medical fluid injector.

In other embodiments, at least one of the fluid inlet path and the fluid outlet path may include a one-way check valve. For example, when the fluid inlet path includes a one-way check valve, the valve may be configured to allow fluid flow into the syringe during a filling process but prevent fluid from flowing out through the fluid inlet path during a fluid delivery process. When the fluid outlet path includes a one-way check valve, the valve may be configured to allow fluid flow out of the syringe during a delivery process but prevent fluid from flowing into the syringe from the fluid outlet path during a fluid filling operation. According to various embodiments, the one-way check valve may be spring loaded or biased to control the pressure at which the one-way check valve opens to allow fluid communication. In various embodiments, the one-way check valve may be a high pressure crack valve.

Figure 3:
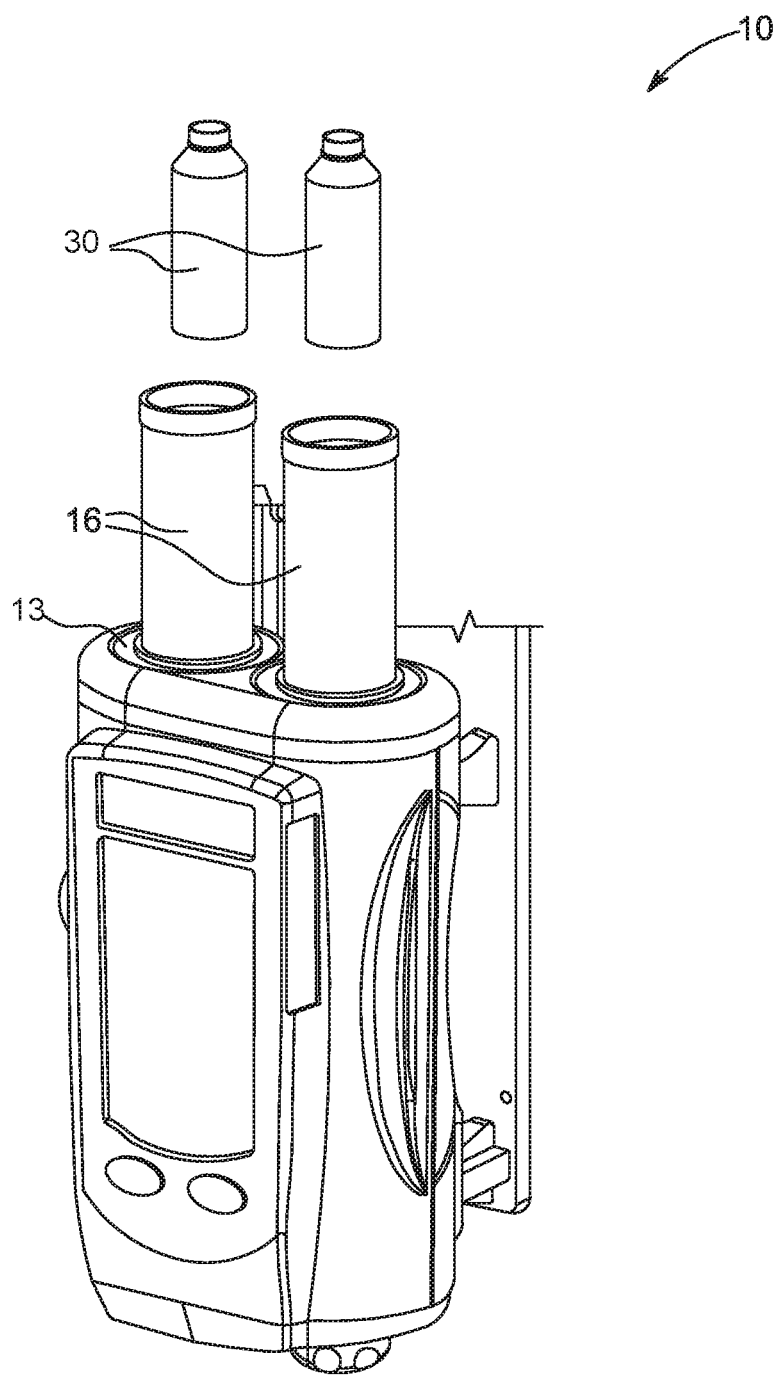
FIG. 3 is a perspective view of a fluid delivery system with pressure jackets for use with a rolling diaphragm syringe and syringe cap according to another example of the present disclosure.

According to certain embodiments, the fluid injector 10 may include at least one syringe including a compressible sidewall, for example, a rolling diaphragm 30, configured to be filled with a fluid and to administer the fluid to a patient during a fluid injection procedure (see, e.g., FIG. 3). The fluid injector may be configured to receive the at least one syringe within at least one pressure jacket 16. The pressure jacket is typically a reusable component configured to be releasably engaged with a fluid injector port, while the syringe is typically a single-use component configured to be discarded after an injection procedure. The fluid injector may have at least one bulk fluid source for filling the at least one syringe with a fluid, for example through the fluid inlet path. The bulk fluid source may be a first bulk fluid source (not shown) containing a first medical fluid, such as an imaging contrast medium, and a second bulk fluid source (not shown) containing a second medical fluid, such as saline, for filling a first and second syringe with first or second fluid contained in the first and second bulk fluid sources, respectively. At least one fluid path set 17 may be fluidly connected with a fluid outlet path of the cap on a distal discharge end of the syringe for delivering fluid from the syringe through tubing connected to a catheter, needle, or other fluid delivery connection (not shown) inserted into a patient at a vascular access site. Fluid flow into and from the syringe may be regulated by a fluid control module (300) associated with the fluid injector and by proximal or distal movement of the syringe causing slidable movement of the outer cap assembly relative to the inner cap assembly of the cap. The fluid control module may operate various pistons and/or flow regulating structures to regulate the delivery of the medical fluid, such as saline solution and contrast, to the patient based on user selected injection parameters, such as injection flow rate, duration, total injection volume, and/or ratio of contrast media and saline. Examples of suitable front-loading fluid injectors that may be used or modified for use with the herein-described system, including at least one pressure jacket and syringe, are disclosed in International Application Publication Nos. WO 2015/164783 and WO 2016/172467, the disclosures of which are incorporated herein by reference.

With reference to FIG. 1, a fluid injector 10 (hereinafter referred to as "injector 10"), such as an automated or powered fluid injector, is adapted to interface with and actuate one or more syringes 12 (hereinafter referred to as "syringe 12"), which may be filed with a fluid F, such as contrast media, saline solution, or any desired medical fluid. The injector 10 may be used during a medical procedure to inject the medical fluid into the body of a patient by driving a plunger 14 of each syringe 12 with a drive member, such as piston 19 (shown in FIG. 2), such as linear actuator or a piston element. The injector 10 may be a multi-syringe injector having two, three or more syringes, wherein the several syringes 12 may be oriented in a side-by-side or other relationship and may be separately actuated by respective drive members/pistons 16 associated with the injector 10. In examples with two or more syringes, for example, arranged in a side-by-side or other relationship and filled with two different fluids, the injector 10 may be configured to deliver fluid from one or both of the syringes 12, sequentially or concurrently. According to one embodiment, the fluid injector 10 may be a dual head injector having two syringes 12a and 12b, a first syringe 12a for delivering a contrast media or other medical fluid and a second syringe 12b for delivering saline or other medically approved flushing agent to flush the contrast media to the patient. In other embodiments, the fluid injector 10 may have three syringes 12, a first and second syringe for delivering one or two different contrast media or other medical fluid and a third syringe for delivering saline or other medically approved flushing agent to flush the contrast media to the patient. According to various embodiments, the fluid injector 10 may be configured to deliver the contrast and saline separately (e.g., delivering a specific volume saline over a specific time followed by delivering a specific volume of contrast over a specific time, followed by a second volume of saline over a specified time to flush the contrast media from the tubing into the patient). According to various embodiments, the fluid injector 10 may be configured to deliver the contrast and saline separately or as a mixture (e.g., delivering a specific volume saline over a specific time followed by delivering a specific volume of contrast or a specified ratio of contrast and saline (i.e., in a "dual flow" process) over a specific time, followed by a second volume of saline over a specified time to flush the contrast media from the tubing into the patient). A technician may program a specific injection protocol into the injector (or use a pre-written protocol) to deliver the desired volumes of saline, contrast, specific ratios of contrast and saline mixtures, etc., at a desired flow rate, time, and volume for each solution. The fluid injector 10 may have at least one bulk fluid source (not shown) for filling the syringes 12 with fluid and in certain embodiments, the fluid injector 10 may have a plurality of bulk fluid source, one for each of the plurality of syringes, for filling each of the plurality of syringes with the desired fluid.

A fluid path set 17 may be in fluid communication with each syringe 12 to place each syringe in fluid communication with a catheter for delivering the fluid F from each syringes 12 to a catheter (not shown) inserted into a patient at a vascular access site. In certain embodiments, fluid flow from the one or more syringes 12 may be regulated by a fluid control module (300) that operates various drive members, valves, stopcocks, and flow regulating structures to regulate the delivery of the saline solution and contrast to the patient based on user selected injection parameters, such as injection flow rate, duration, total injection volume, and ratio of fluids from the syringes 12, including specific ratios of each fluid in a dual flow injection protocol.

Figure 2:
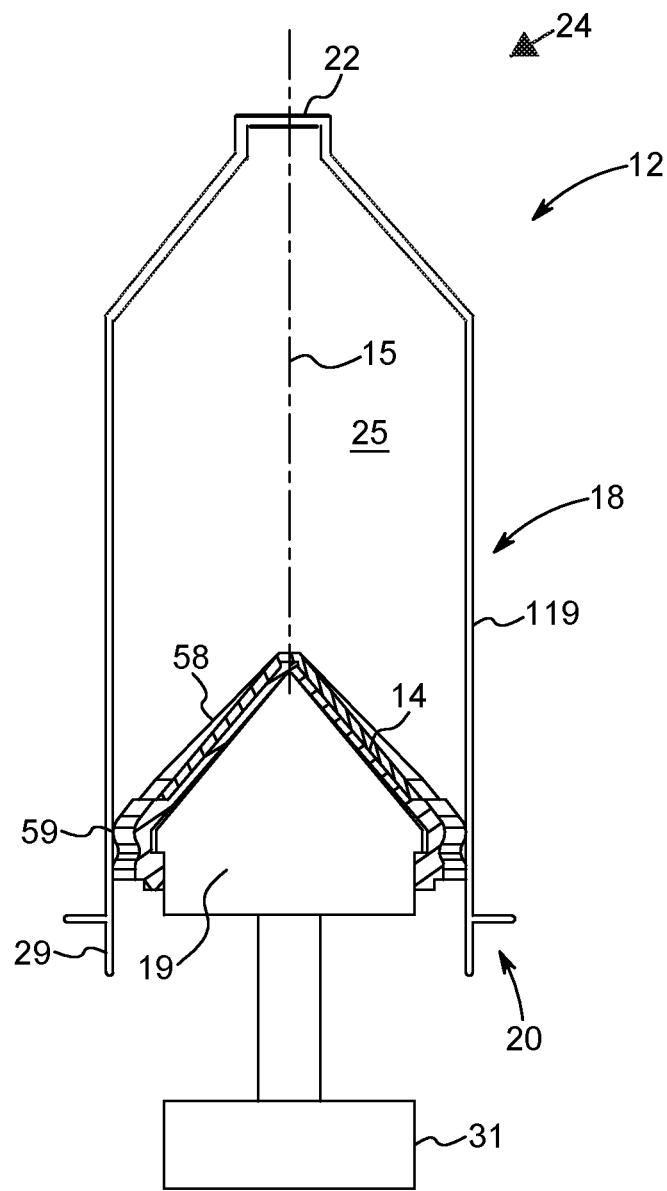
FIG. 2 is a side cross-sectional view of a syringe configured for use with syringe cap according to various embodiments and the fluid delivery system of FIG. 1.

With reference to FIG. 2, the drive member 19, such as a reciprocally driven piston moved by a motor 31, may be configured to extend into and from the respective syringe port 13 through an opening in the front end of the injector housing. In fluid injector embodiments comprising a plurality of syringes, a separate drive member/piston 19 may be provided for each syringe 12. Each drive member/piston 19 is configured to impart a motive force to at least a portion of the syringe 12, such as the plunger 14 or a distal end of a rolling diaphragm syringe (for example, as described in PCT/US2017/056747; WO 2016/172467; and WO 2015/164783, the disclosures of which are incorporated herein by this reference). The drive member or piston 19 may be reciprocally operable via electro-mechanical drive components such as a ball screw shaft driven by the motor 31, a voice coil actuator, a rack-and-pinion gear drive, a linear motor, a linear actuator, and the like. The motor 31 may be an electric motor.

Examples of suitable front-loading fluid injectors 10 are disclosed in U.S. Pat. Nos. 5,383,858; 7,553,294; 7,666,169; 9,173,995; 9,199,033; and 9,474,857; and in PCT Application Publication No. WO 2016/191485 and WO 2016/112163, the disclosures of which are incorporated by reference in their entirety.

Having described the general structure and function of specific embodiments of the fluid injector 10, an embodiment of syringe 12 configured for use with the injector 10 will now be described with reference to FIG. 2. The syringe 12 generally has a cylindrical syringe barrel 18 formed from glass, metal, or a suitable medical-grade plastic, desirably a clear or substantially translucent plastic material. The material of the syringe 12 is desirably selected to meet the required tensile and planar stress requirements, water vapor transmission, and chemical/biological compatibility. The barrel 18 has a proximal end 20 and a distal end 24, with a sidewall 119 extending therebetween along a length of a longitudinal axis 15 extending through a center of the barrel 18. In some examples, the distal end 24 may have a conical shape that narrows in a distal direction from the cylindrical barrel 18. A fluid nozzle 22 extends from the distal end 24. The barrel 18 has an interior volume 25 configured for receiving the fluid therein. The proximal end 20 of the barrel 18 may be sealed with the plunger 14 that is reciprocally movable through the barrel 18 by reciprocal movement of the corresponding piston 19 or drive member.

In some examples, the proximal end 20 of the syringe 12 can be sized and adapted for being removably inserted in a syringe port 13 of the injector 10 (shown in FIG. 1). In some examples, the proximal end 20 of the syringe 12 defines an insertion section 29 that is configured to be removably inserted into the syringe port 13 of the injector 10 while the remaining portion of the syringe 12 remains outside of the syringe port 13.

In some examples, such as shown in FIG. 3, the injector 10 may be configured for receiving and retaining a pressure jacket 16 within each syringe port 13 of the injector 10. While FIGS. 1 and 3 illustrate fluid injectors 10 with two syringe ports 13, which for the injector 10 shown in FIG. 3 each having a corresponding pressure jacket 16, other examples of the fluid injector 10 may include a single syringe port 13 and optionally, a corresponding pressure jacket 16 or more than two syringe ports 13 with an optional corresponding number of pressure jackets 16. In embodiments comprising pressure jackets, each pressure jacket 16 may be configured to receive a syringe, such as a syringe for an angiographic (CV) procedure, or a rolling diaphragm syringe 30 (suitable examples of which are described in described in PCT/US2017/056747; WO 2016/172467; and WO 2015/164783). A fluid path set, similar to the fluid path set 17 shown in FIG. 1, may be fluidly connected with a discharge end of each rolling diaphragm syringe 30 for delivering fluid from the syringes 30 through tubing connected to a catheter, needle, or other fluid delivery connection (not shown) inserted into a patient at a vascular access site. According to various embodiments, the syringe 12 or 30 may be a pre-filled syringe, i.e., the syringe may be prefilled with a medical fluid, such as a contrast agent or saline, when provided by the syringe manufacturer. According to certain embodiments, the pre-filled syringe may be required to be spiked or otherwise punctured at the discharge end prior to an injection procedure to allow fluid to be expelled from the syringe into a fluid line to the patient, as described herein.

Figure 4A:
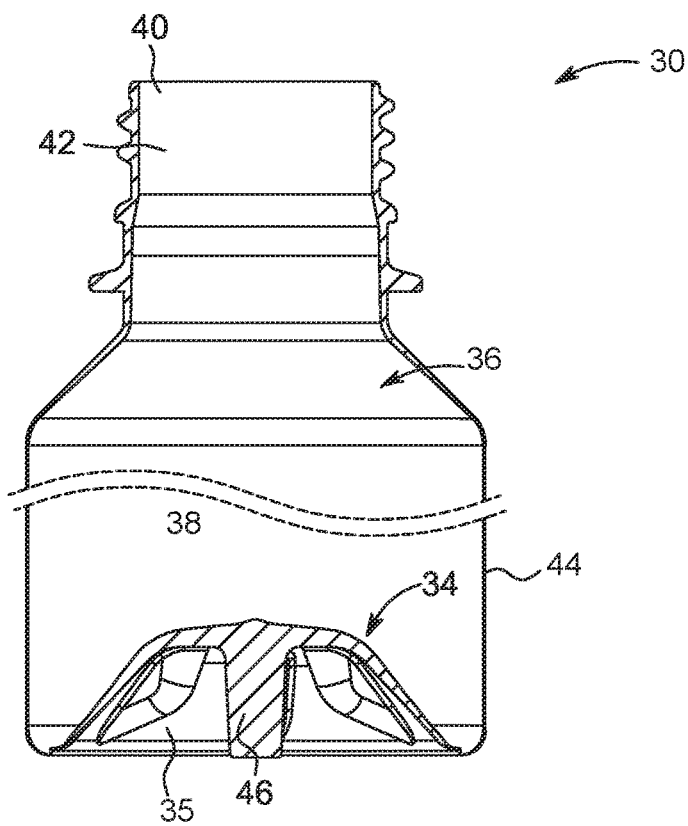
FIGS. 4A and 4B are side cross-sectional views of a rolling diaphragm syringe configured for use a syringe cap according to various embodiments and with the fluid delivery system of FIG. 3.
Figure 4B:
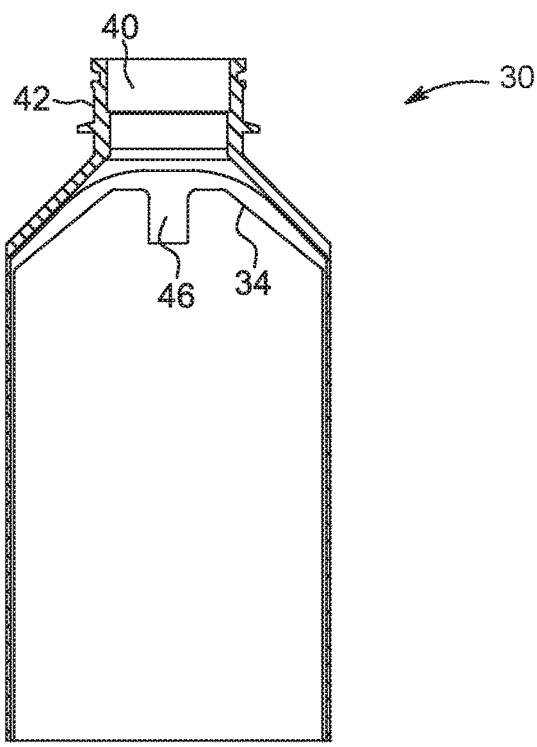

With reference to FIG. 4A and 4B, the rolling diaphragm syringe 30 generally includes a hollow body 36 defining an interior volume 38. The body 36 has a forward or distal end 40, a rearward or proximal end 35, and a flexible sidewall 44 extending therebetween. The proximal end 35 may be configured to act as piston to pressurize the syringe interior to draw in or expel fluid therefrom, as described herein. The sidewall 44 of the rolling diaphragm syringe 30 defines a soft, pliable or flexible, yet self-supporting body that is configured to roll upon itself, as a "rolling diaphragm", under the action of the a drive member or piston of the fluid injector 10. The drive member/piston 19 may be configured to releasably engage a drive member engagement portion 46 at the proximal end 35 of the rolling diaphragm syringe 30 (examples of which are described in PCT/US2017/056747). In operation, the sidewall 44 is configured to roll such that its outer surface is folded and inverted in a radially inward direction as the drive member/piston 19 moves the proximal end 35 in a distal direction and unrolled and unfolded in the opposite manner in a radially outward direction as the drive member/piston 19 retract the proximal end 35 in a proximal direction.

With continued reference to FIG. 4A and 4B, the rearward or proximal portion of the sidewall 44 connects to a closed end wall 34, and a forward or distal portion of the sidewall 44 defines a discharge neck 42 opposite the closed end wall 34. The closed end wall 34 may have a concave shape to facilitate the initiation of the inversion or rolling of the sidewall 44, enhance mechanical strength of the closed end wall 34, and/or to provide a receiving pocket to receive a distal end of drive member/piston 19. For example, the closed end wall 34 may define a receiving end pocket for interfacing directly with a similarly-shaped distal end of the drive member/piston 19. In some examples, at least a portion of the drive member/piston 19 may be shaped to substantially match the shape of the closed end wall 34 or, alternatively, pressure from the drive member/piston 19 as it is moved distally may conform the end wall 34 to substantially match the shape of at least a portion of the drive member/piston 19.

The end wall 34 may have a central portion having a substantially dome-shaped structure and a drive member engagement portion 46 extending proximally from the central portion. The drive member engagement portion 46 is configured for releasably interacting with a corresponding engagement mechanism on the drive member/piston 19 of the fluid injector 10, for example as the drive member/piston is retracted. The rolling diaphragm syringe 30 may be made of any suitable medical-grade plastic or polymeric material, desirably a clear or substantially translucent plastic material. The material of the rolling diaphragm syringe 30 is desirably selected to meet the required tensile and planar stress requirements, water vapor transmission, and chemical/biological compatibility In certain embodiments of the present disclosure, pressure jackets having a one-piece design are described, where the syringe is inserted into the pressure jacket from the distal end of the pressure jacket. The neck of the syringe may protrude from the distal end of the pressure jacket such that the syringe may be connected to fluid lines leading to the patient. A proximal end of the pressure jacket is typically retained on the fluid injector by a coupling member. During an injection procedure, an exterior wall of the syringe expands against an interior wall of the pressure jacket due to the forces that act on the syringe in a radially outward direction. Additionally, the syringe may experience significant axial movement during a high pressure injection due to the axial movement of the piston acting on the syringe. Such axial movement of the syringe is undesirable and may lead to inaccurate volume delivery.

Figure 5:
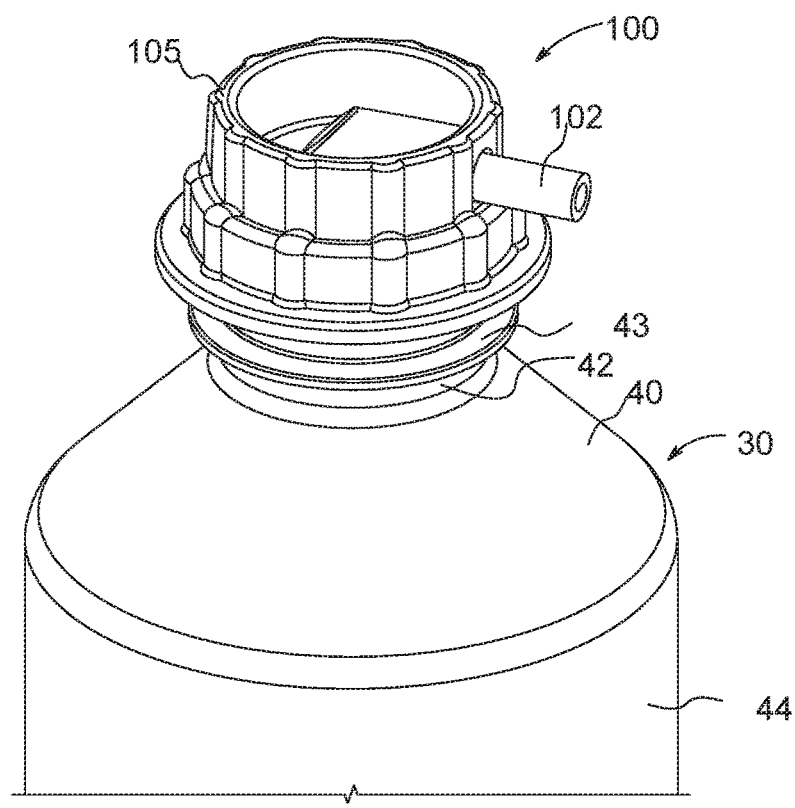
FIG. 5 is a top perspective view of a syringe and filling cap in accordance with one example of the present disclosure.
Figure 6:
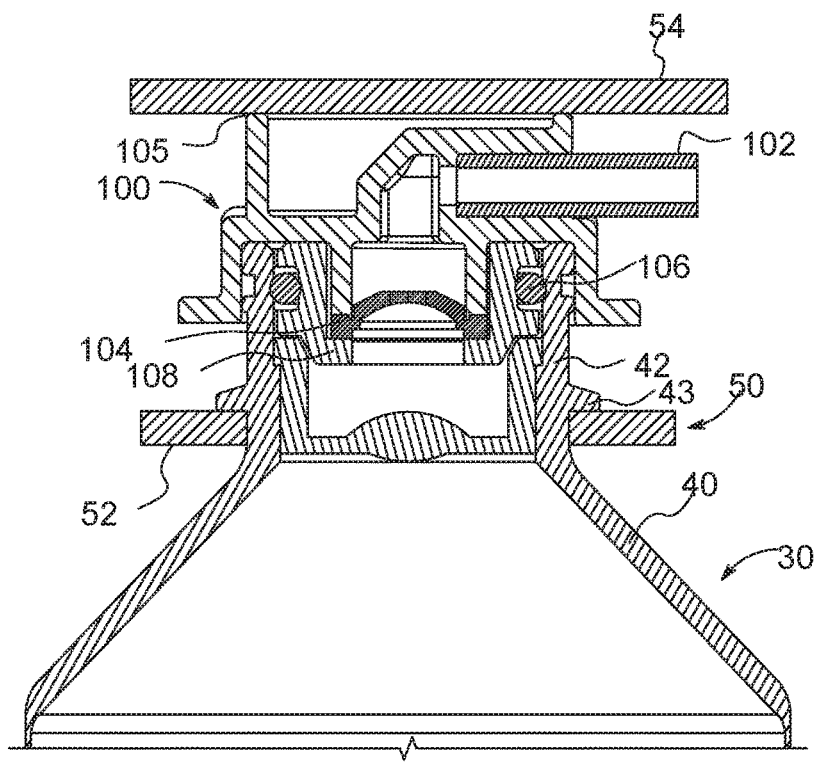
FIG. 6 is a cross-sectional view of the syringe and filling cap of FIG. 5 shown with syringe retaining features configured to prevent axial movement of the syringe.

With reference to FIGS. 5 and 6, a rolling diaphragm syringe 30 for use with a fluid injector described herein generally includes a hollow body that includes a forward or distal end 40, a rearward or proximal end (not shown), and a flexible sidewall 44, such as a rolling diaphragm, extending therebetween. In use, the proximal end is configured for insertion into the throughbore of a pressure jacket such that the sidewall 44 is surrounded by the interior surface of the pressure jacket. At least a portion of the distal end 40 of the syringe 30 may be exposed from a distal end of the pressure jacket 16. In some examples, the syringe 30 may be formed using a blow-molding technique. In other examples, the syringe 30 may be injection molded.

The distal end 40 of the syringe 30 defines a discharge neck 42 opposite a closed end wall 34 at the proximal end thereof. The distal end 40 may have a frusto-conical shape that gradually narrows from the sidewall 44 to the discharge neck 42. A retention flange 43 may extend around the circumferential surface of the discharge neck 42. The retention flange 43 may extend around the entire circumferential surface of the discharge neck 42 or at least a portion of the circumferential surface of the discharge neck 42. The retention flange 43 may have a proximal surface 45 for interacting with a corresponding feature of the fluid injector to limit the distance that the syringe slides in the proximal direction when the end wall 34 is retracted in the proximal direction. The proximal end of the syringe 30 may be shaped to interface directly with a drive member of the fluid injector 10. The sidewall 44 of the syringe 30 defines a soft, pliable or flexible, yet self-supporting body that is configured to unroll and roll in upon itself as a rolling diaphragm under the action of the drive member. In particular, the sidewall 44 of the syringe 30 is configured to roll such that its outer surface is folded and inverted in a radially inward direction as the drive member is moved in a distal direction, and unroll and unfold in the opposite manner in a radially outward direction as the drive member is retracted in a proximal direction.

With continued reference to FIGS. 5 and 6, a filling cap 100 may be provided on the discharge neck 42 of the syringe 30 to permit flow of fluid into the syringe 30. The filling cap 100 is removably connected to the discharge neck 42 of the syringe 30 via a threaded connection, a snap-fit connection, a friction-fit connection, or any other suitable removable connection. In some examples, an optionally removable clip may be provided for connecting the filling cap 100 to the discharge neck 42 of the syringe 30. The filling cap 100 includes an inlet port 102 configured for connection to tubing from a bulk fluid source to permit fluid to be transferred from the bulk fluid source to the syringe 30. The inlet port 102 may be located on a radial side of the filling cap 100. A crack pressure valve 104 is provided in the filling cap 100 to permit flow of fluid through the filling cap 100 into the syringe 30 when a crack pressure is exceeded, while preventing flow through the filling cap 100 when the head height of pressure is less than the crack pressure. In one example, the crack pressure valve 104 may be a slit valve or other conventional crack pressure valve. The filling cap 100 also includes at least one gasket 106 around an outer surface of the filling cap 100. The gasket 106 is configured to create a liquid-tight seal between an interior surface of the discharge neck 42 and the filling cap 100. A base member 108 in the filling cap 100 may hold the gasket 106 against the inner surface of the discharge neck 42. The base member 108 may also hold the crack pressure valve 104 within the filling cap 100. In one example, the components of the filling cap 100 may be molded integrally with one another as a monolithic structure. In another example, the components of the filling cap 100 may be connected to one another by welding, adhesive, interference fit, one or more fasteners, or a combination thereof. The distal surface 105 of the filling cap 100 may be configured as a substantially flat surface, for example around the circumference of the distal end of the filling cap 100. The flat surface 105 may be configured to interact with a retaining surface of a holding bracket 54 to retain the filling cap 100 in the discharge neck 42 during a filling procedure. A flow controller may also be provided in the filling cap 100 and sized and shaped so as to encourage the fluid flowing thereon to adhere to an inner surface of the syringe 30 in accordance with the Coandă effect. The Coandă effect is the tendency for a fluid jet to be attracted to a nearby surface. Thus, as fluid flows down the flow controller into the syringe 30, it is naturally attracted to the inside surface of the syringe 30. This flow along the inside surface of the syringe 30 helps to reduce turbulence as the fluid fills the syringe 30, which aides in reducing air bubbles from forming as the syringe 30 is filled.

Figure 7:
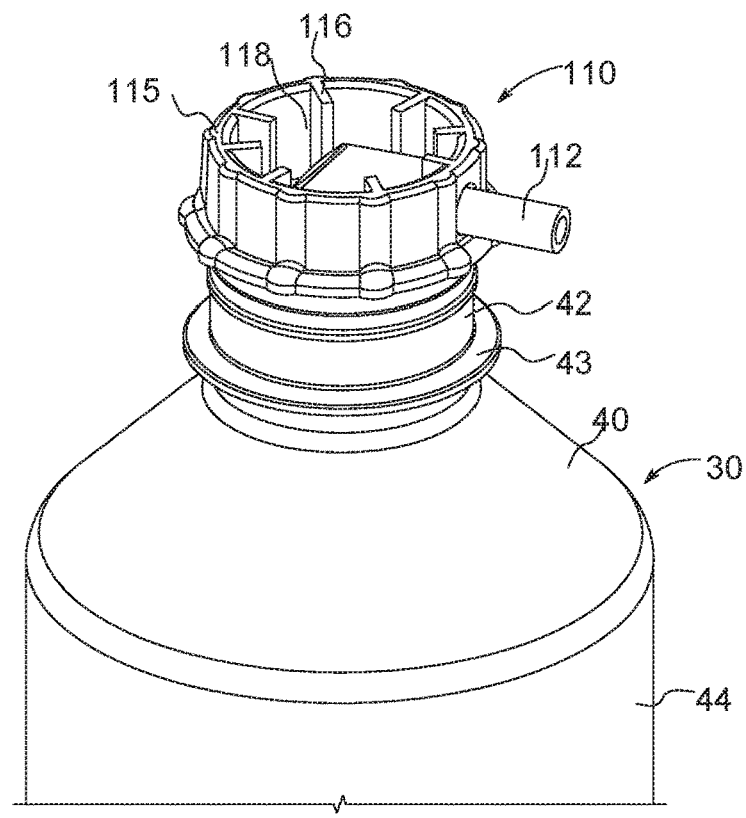
FIG. 7 is a top perspective view of a syringe and dispensing cap in accordance with one example of the present disclosure.
Figure 8:
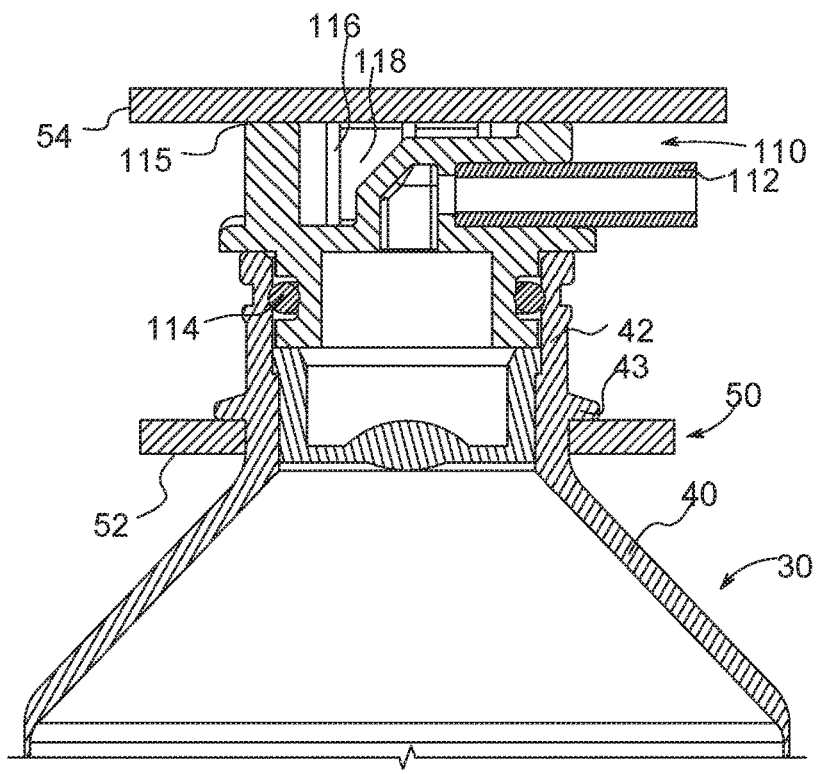
FIG. 8 is a cross-sectional view of the syringe and dispensing cap of FIG. 7 shown with syringe retaining features configured to prevent axial movement of the syringe.

With reference next to FIGS. 7 and 8, a dispensing cap 110 may be provided on the discharge neck 42 of the syringe 30 to permit dispensing of fluid from the syringe 30 after the syringe 30 has been filled with fluid from a bulk fluid source. The dispensing cap 110 is removably connected to the discharge neck 42 of the syringe 30 via a threaded connection, a snap-fit connection, a friction-fit connection, a gasket seal fit, or any other suitable removable connection. In some examples, an optionally removable clip may be provided for connecting the dispensing cap 110 to the discharge neck 42 of the syringe 30. The dispensing cap 110 includes an outlet port 112 configured for connection to tubing to a catheter, needle, or other fluid delivery connection (not shown) inserted into a patient at a vascular access site to deliver fluid from the syringe 30 to the patient. The outlet port 112 may be located on a radial side of the dispensing cap 110. The dispensing cap 110 also includes a gasket 114 around an outer surface of the dispensing cap 110. The gasket 114 is configured to create a liquid-tight seal between an interior surface of the discharge neck 42 and dispensing cap 110.

With continued references to FIGS. 7 and 8, the dispensing cap 110 includes a plurality of ribs 116 extending from an interior surface of a sidewall defining the cap perimeter. The cap perimeter and the ribs 116 may provide a substantially flat distal surface 115 configured to interact with a retaining surface of a holding bracket 54 to retain the dispensing cap 110 in the discharge neck 42 during a dispensing procedure. The ribs 116 protrude into a cavity 118 defined by the sidewall of the dispensing cap 110. In one example, the ribs 116 are arranged in a radial configuration around the circumferential surface of the cavity 118. The ribs 116 may extend a length into the cavity 118. In some examples, the ribs 116 may be spaced apart from one another in equal or unequal angular intervals around an interior surface of the cap sidewall. In one example, the ribs 116 extend into the cavity 118 to meet at a central point in the cavity 118. In another example, the ribs 116 are configured in a "waffle" or lattice configuration in the cavity 118. The ribs 116 are provided in the dispensing cap 110 to provide additional surface area and structural support upon which a syringe retaining mechanism (described herein) may contact the dispensing cap 110 when engaged with the syringe 30. The increased surface area spreads the retaining force over a larger surface of the dispensing cap 110 in order to reduce stress points in the dispensing cap 110 due to the pressures that are experienced by the syringe 30 during the dispensing process. In some examples, at least a portion of the cap sidewall or the ribs 116 may be recessed axially in the proximal direction relative to the remaining portions of the sidewall or the ribs 116, for example around fluid outlet port 112, in order to reduce localized forces in predetermined portions of the dispensing cap 110.

With reference to the various embodiments of the syringe caps described herein, as illustrated in FIGS. 5-13, a syringe retaining mechanism, such as a holding brace 50 and/or a holding bracket 54 or any of the syringe retaining mechanisms described in U.S. Provisional Application No. 62/729,642, entitled "Injector Syringe Interface," filed on 11 Sep. 2018, is provided on the fluid injector to retain the syringe 30 in the pressure jacket 16 or in a syringe port, for example to limit axial distal and/or proximal movement of the syringe 30 during filling and/or dispensing of fluid to within the distance limits for the slidable cap assembly described herein. The holding brace 50 may include a recessed member 52 configured to engage the discharge neck 42 and/or radial flange 43 of the corresponding syringe 30. The recessed member 52 may include a recess that corresponds in shape and dimension to the discharge neck 42 of the syringes 30. The holding brace 50 may move between an open position in which the holding brace 50 is removed from the syringe 30, and a closed position in which the holding brace 50 is engaged with the discharge neck 42 of the syringe 30. In the closed position, the recessed member 52 may engage the discharge neck 42 below the flange 43 to limit the distance that syringe 30 may be pulled into the pressure jacket during a filling process of the syringe 30 when the syringe 30 is in a compressed state. In one example, the movement of the holding brace 50 between the open position and the closed position may be automated by a controller associated with the fluid injector. In another example, movement of the holding brace 50 between the open position and the closed position may be actuated manually by a user. The arms of the holding brace 50 may include tapered surfaces that assist in indexing the syringe 30 a desired position in the fluid injector. Using this configuration, regardless of the vertical orientation of the syringe 30 in the fluid injector, the tapered surfaces work to index the syringe 30 at the proper vertical height. In another aspect, the holding bracket 54 may restrain a wedge (not shown) on the holding brace 50 to index distally to seat.

According to various embodiments, the holding bracket 54 may be movable between a first, closed position and a second, open position. In the closed position, the holding bracket 54 engages the distal ends 34 of one of the filling cap 100, the dispensing cap 110, or a retention flange 43 to retain the syringe 30 longitudinally within the pressure jacket 16 and limit movement of the syringe 30 in an axial direction relative to the pressure jacket 16 during an injection procedure. In certain aspects, the holding bracket 54 may counteract at least a portion of the pressure associated with the piston moving the proximal end of the syringe 30 during an injection procedure. In the open position, the holding bracket 54 moves away from contacting the filling cap 100 or the dispensing cap 110, such as raising upward relative to the caps or by moving laterally away from the caps, to allow the syringe 30 to be inserted/removed from the pressure jacket 16. In some examples, the holding bracket 54 may pivot between the open position and the closed position. In other examples, the holding bracket 54 may be stationary, while the at least one pressure jacket 16, along with the syringe 30 is moved relative to the holding bracket 54 to engage the distal end 34 of the syringe 30 with the holding bracket 54. The holding bracket 54 assists in indexing the caps 100, 110 in the correct orientation in the fluid injector. Using this configuration, regardless of the axial position of the caps 100, 110 when placed on the syringe 30, the holding bracket 54 contacts the caps 100, 110 to move them axially in a proximal direction. Such axial movement of the caps 100, 110 can be controlled such that the caps 100, 110 are in each instance placed in the same position on the distal end 34 of the syringe 30 to assure a proper seal with the syringe 30. The interaction of the holding bracket 54 and the flat distal surface 105 and/or 115 of the filling cap 100 and/or dispensing cap 110, respectively, may eliminate the need for an engaging interaction between a pressure jacket and a separate pressure jacket cap to maintain the syringe 30 within the pressure jacket during a filling and/or injection procedure. The combination of the dispensing cap 110 and the holding bracket 54 may counteract up to about 600 psi of pressure that is applied to the proximal end of the syringe 30 during an injection procedure or priming/purging procedure.

With reference again to FIGS. 5 to 8, operation of the holding bracket 54 and the holding brace 50 is now described. As shown in FIGS. 1 and 2, the filling cap 100 is connected to the discharge neck 42 of the syringe 30. After the filling cap 100 has been connected to the syringe 30, the holding brace 50 and the holding bracket 54 are independently or simultaneously moved into the closed position to contact the proximal end of the flange 43 and the distal end of the filling cap 100, respectively. The holding brace 50 assists in retaining the syringe 30 from moving proximally into the pressure jacket 16 during the filling procedure, while the holding bracket 54 retains the syringe 30 from moving distally during an injection procedure.

As shown in FIGS. 6 and 8, before, after, or during the movement of the holding bracket 54 into engagement with the filling cap 100, the holding brace 50 is extended to engage the discharge neck 42 of the syringe 30. The holding brace 50 is extended and positioned to engage the discharge neck 42 against a proximal surface of the flange 43. The holding bracket 54 engages the distal surface of the filling cap 100 and moves the filling cap 100 to a position where the filling cap 100 is fully engaged with the distal end 34 of the syringe 30. In use, the holding brace 50 is configured to prevent axial movement of the syringe 30 in a proximal direction when the syringe 30 is being filled with fluid. During such procedure, the drive member of the fluid injector pulls the end wall of the syringe 30 in a proximal direction with a force between 10 to 300 lbs. The holding brace 50 restrains the distal end 34 of the syringe 30 from moving in the proximal direction due to engagement of the holding brace 50 with the proximal surface of the flange 43 of the syringe 30. In this manner, movement of the syringe 30 in the proximal direction relative to the pressure jacket can be prevented. After filling the syringe 30, the holding bracket 54 may be lifted, manually or automatically, from the second (closed) position to the first (open) position by reversing the steps described herein. In some examples, movement of the holding bracket 54 from the second (closed) position to the first (open) position may automatically remove the filling cap 100 in preparation for dispensing fluid from the syringe 30.

The fluid dispensing operation can be carried out in a manner similar to the filling operation, where the holding bracket 54 is moved from the first (open) position to the second (closed) position to contact the dispensing cap 110.

Figure 9A:
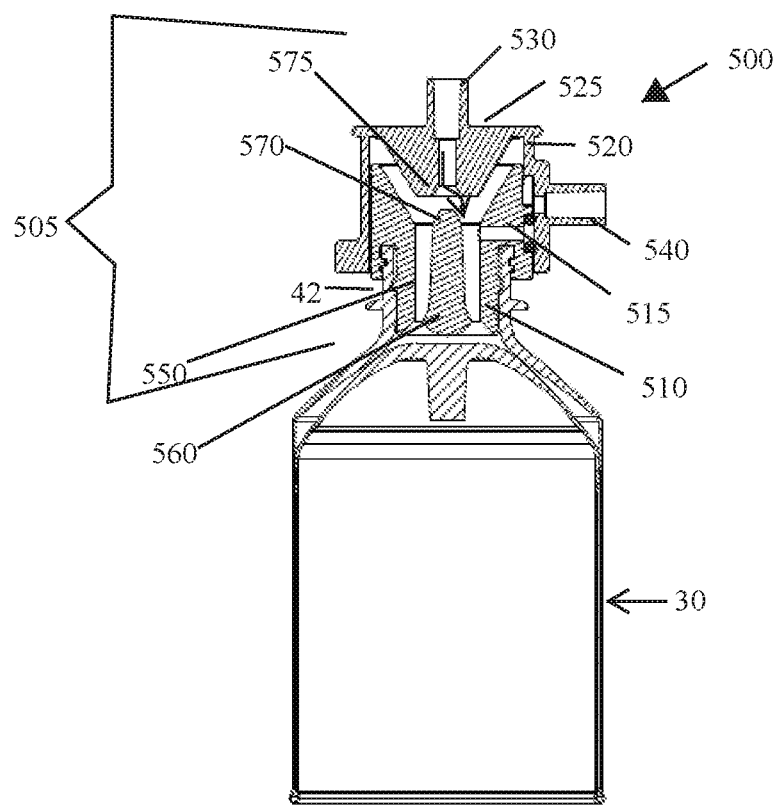
FIGS. 9A and 9B illustrate a sliding syringe cap having separate filling and delivery paths according to an embodiment.
Figure 9B:
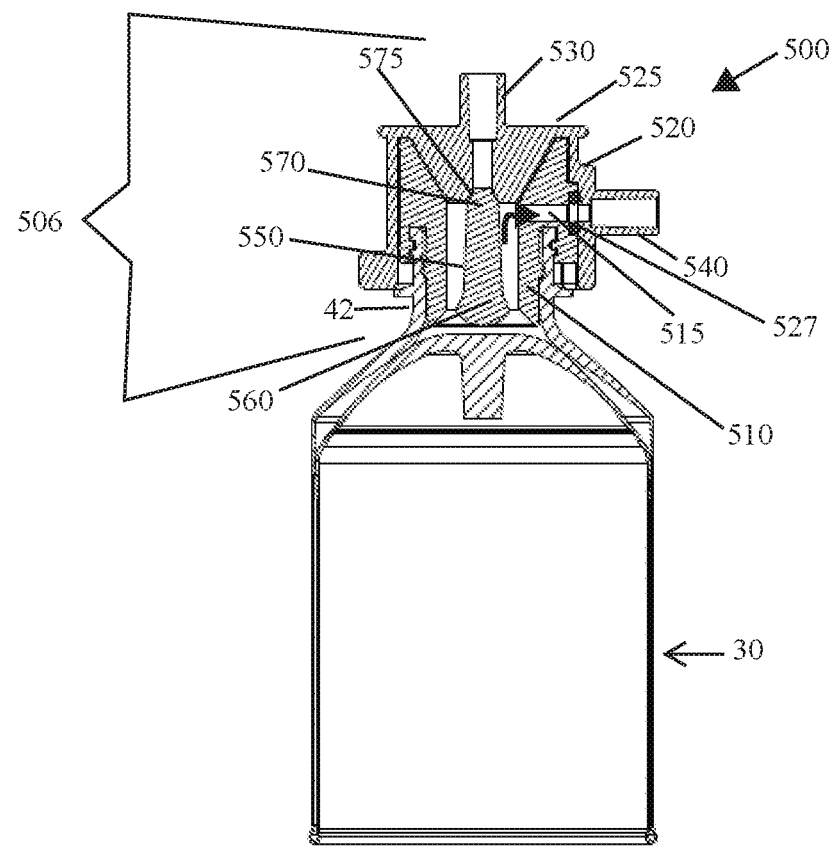

In another embodiment the syringe cap may be configured to switch or slide between a first filling position 505 and a second delivery position 506. With reference to FIGS. 9A and 9B, one aspect of a sliding syringe cap 500 is described. Referring first to FIG. 9A, a sliding syringe cap 500 is shown in the first filling position 505. Sliding syringe cap 500 is shown in fluid tight connection with the distal discharge neck 42 of rolling diaphragm syringe 30. The fluid tight connection may be affected by use of an O-ring or other fluid sealing arrangement, and/or the inner cap assembly 510 may be in frictional fit, adhered or laser welded, screw fit, or otherwise attached to the discharge neck 42 of syringe 30. Sliding cap 500 comprises an inner cap assembly 510 in slidable engagement with an outer cap assembly 520. The inner cap assembly 510 includes an inner delivery fluid path 515, a syringe fluid path 550, a pin 570, and a flow controller 560. The outer cap assembly 520 includes a fluid inlet path 530, a fluid outlet path 540, a pin abutment feature 575, and a flat distal surface 525 to interact with a retaining surface of a holding bracket 54. The inner delivery fluid path 515 of the inner cap assembly 510 may include at least one O-ring 527 to provide fluid tight seal between the inner delivery fluid path 515 and the fluid outlet path 540 of the outer cap assembly 520 or the inner surface of the outer cap assembly 520.

Referring to FIG. 9A, a cap in the first filling position 505 is illustrated. In the first filling position 505, fluid communication is established between the fluid inlet path 530 and the interior of the syringe 30 during a filling procedure. A fluid container is attached by a fluid delivery line to the fluid inlet path 530 and fluid may flow into the syringe 30. In particular, the pin 570 and the pin abutment feature 575 are placed in a separated position to allow fluid to flow from the fluid container into the syringe 30. In the first filling position, fluid communication between the inner delivery fluid path 515 and the fluid outlet path 540 is prevented. Fluid flows into the syringe past flow controller 560, which forces the fluid to flow down the inner sidewall of syringe 30.

FIG. 9B illustrates the cap in a second delivery position 506. In the second delivery position 506, the outer cap assembly 520 has slid in a proximally relative to the inner cap assembly 510 to allow fluid communication between the inner delivery fluid path 515, and the syringe 30, and the fluid outlet path 540 via syringe fluid path 550. A fluid tight connection established by O-ring 527. Fluid communication between the fluid inlet path 530 and the syringe fluid path 550 is prevented by abutment of the pin 570 with the pin abutment feature 575.

Figure 10A:
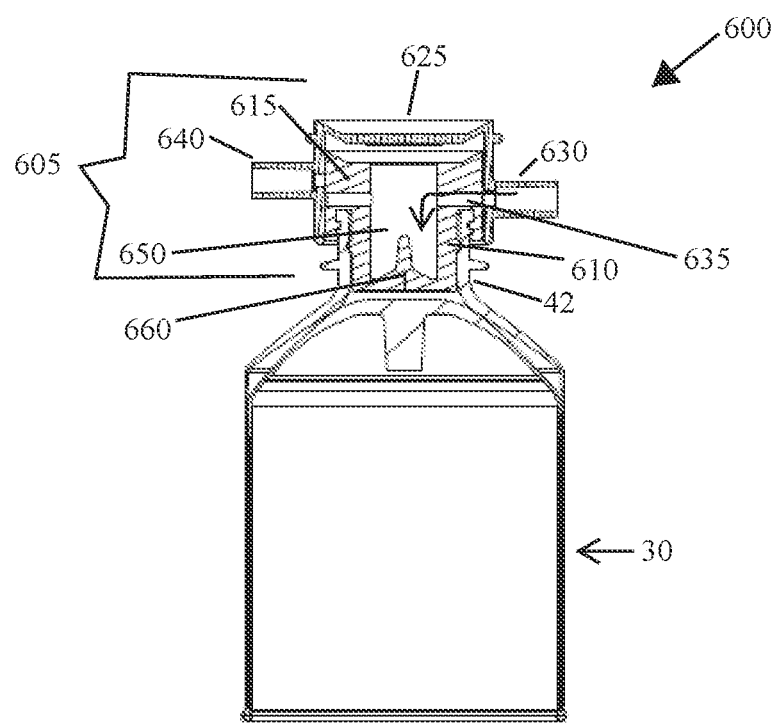
FIGS. 10A to 10C illustrate a sliding syringe cap having separate filling and delivery paths and a separate shut-off position according to an embodiment.
Figure 10B:
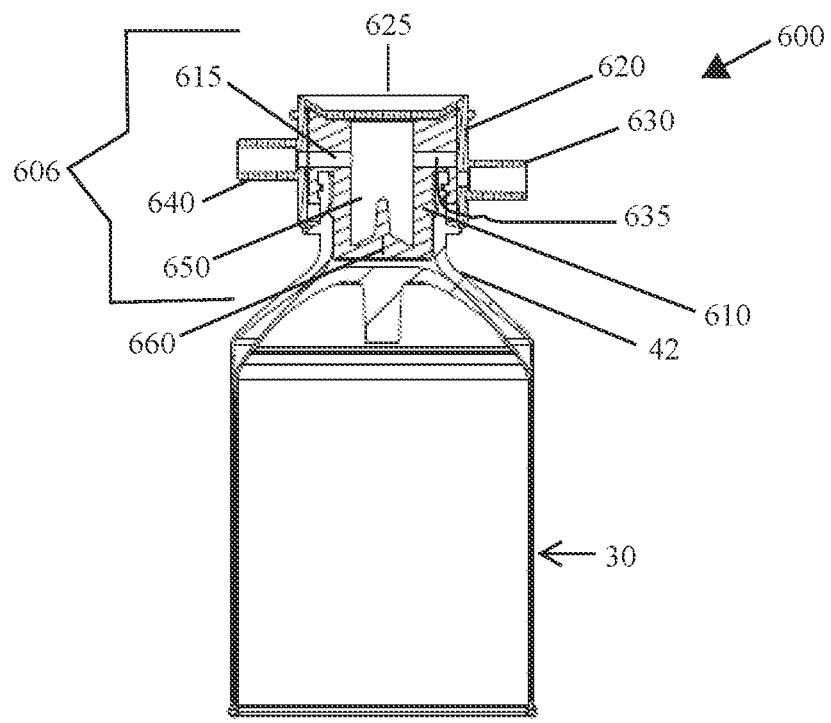
Figure 10C:
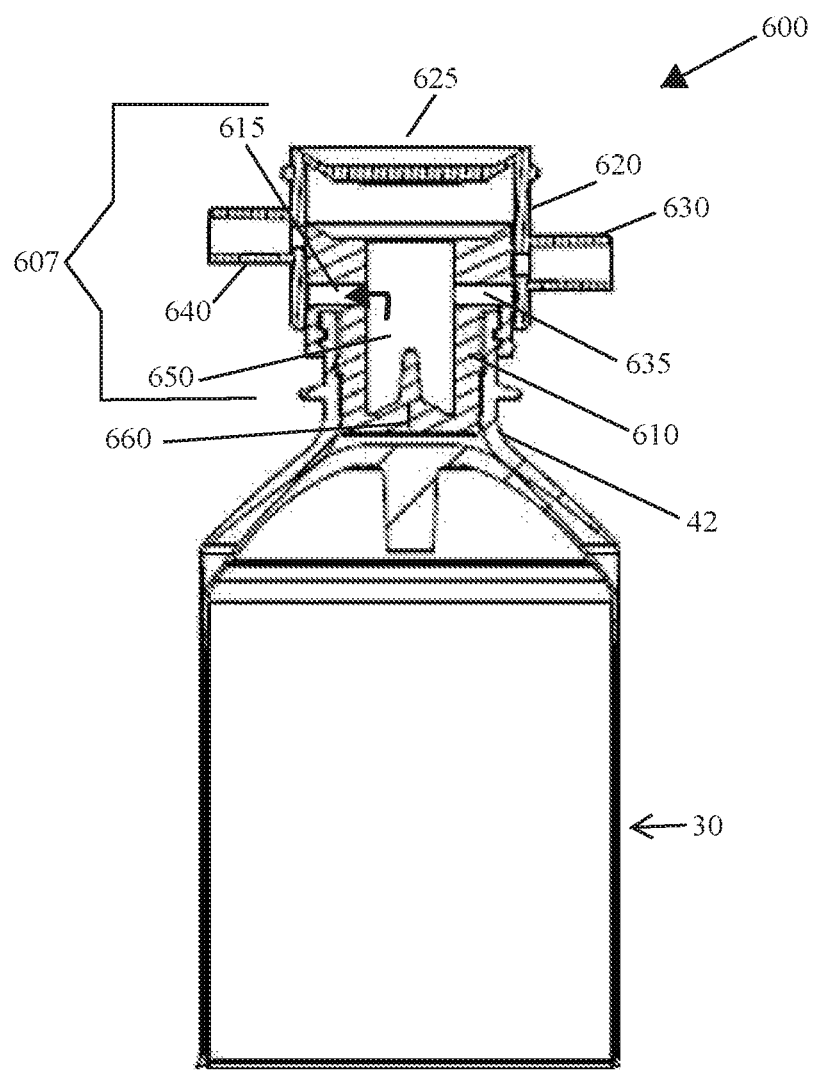

In another embodiment the syringe cap 600 may be configured to switch or slide between a first filling position 605, a second delivery position 606, and a third closed position 607, where fluid communication between the interior of the syringe 30 and either fluid path is prevented. With reference to FIGS. 10A, 10B, and 10C, one aspect of a sliding syringe cap 600 is described. Referring first to FIG. 10A, a sliding syringe cap 600 is shown in the first filling position 605. Sliding syringe cap 600 is shown in fluid tight connection with the distal discharge neck 42 of rolling diaphragm syringe 30. The fluid tight connection may be affected by use of an O-ring or other fluid sealing arrangement, and/or the inner cap assembly 610 may be in frictional fit, adhered or laser welded, screw fit, or otherwise attached to the discharge neck 42 of syringe 30. Sliding cap 600 comprises an inner cap assembly 610 in slidable engagement with an outer cap assembly 620. The inner cap assembly 610 includes an inner filling path 635, an inner delivery fluid path 615, a syringe fluid path 650, and a flow controller 660. The outer cap assembly 620 includes a fluid inlet path 630, a fluid outlet path 640, and a flat distal surface 625 to interact with a retaining surface of a holding bracket 54. In certain embodiments, the inner filling path 635 and the inner delivery fluid path 615 of the inner cap assembly 610 may include at least one O-ring (not shown) to provide fluid tight seal between the inner filling path 635 and the inner delivery fluid path 615 and the fluid inlet path 630 and fluid outlet path 640, respectively, of the outer cap assembly 620 or the inner surface of the outer cap assembly 620.

Referring to FIG. 10A, a cap in the first filling position 605 is illustrated. In the first filling position, fluid communication is established between the fluid inlet path 630 and the interior of the syringe 30 via inner filling path 635 during a filling procedure. A fluid container is attached by a fluid delivery line to the fluid inlet path 630 and fluid may flow into the syringe 30. In particular, fluid communication is established between the fluid inlet path 630 and the inner filling path 635 to allow fluid to flow from the fluid container into the syringe 30. A fluid tight connection may be formed between the fluid inlet path 630 and the inner filling path 635 by an O-ring (not shown) or other sealing feature. In the first filling position, fluid communication between the inner delivery fluid path 615 and the fluid outlet path 640 is prevented. Fluid flows into the syringe past flow controller 660, which forces the fluid to flow down the inner sidewall of syringe 30. Fluid flow from the fluid outlet path 640 may be blocked, for example by a one-way valve 741 or other flow prevention device, such as a valve, stopcock, or clamp.

FIG. 10B illustrates the cap in a second delivery position 606. In the second delivery position, the outer cap assembly 620 has slid in a proximally relative to the inner cap assembly 610 to establish fluid communication between the inner delivery fluid path 615, and the syringe 30, and the fluid outlet path 640 via syringe fluid path 650. A fluid tight connection may be formed between the fluid outlet path 640 and the inner delivery path 615 by an O-ring (not shown) or other sealing feature. In the second delivery position, fluid communication between the inner filling fluid path 635 and the fluid inlet path 630 is prevented.

FIG. 10C illustrates the cap in a third closed position 607. In the third closed position 607, the outer cap assembly 620 has slid in a distally relative to the inner cap assembly 610 to prevent fluid communication between the inner delivery fluid path 615, and the syringe 30, and the fluid outlet path 640 and also prevent fluid communication between the inner filling fluid path 635 and the syringe 30, and the fluid inlet path 630. Accordingly, in the third closed position 607, the inner volume of the syringe is fluidly isolated from either fluid path 630 and 640. Thus, any force applied to the syringe 30 via a piston will increase the pressure of the fluid within the syringe 30 and does not deliver any fluid out of the syringe 30.

Figure 11B:
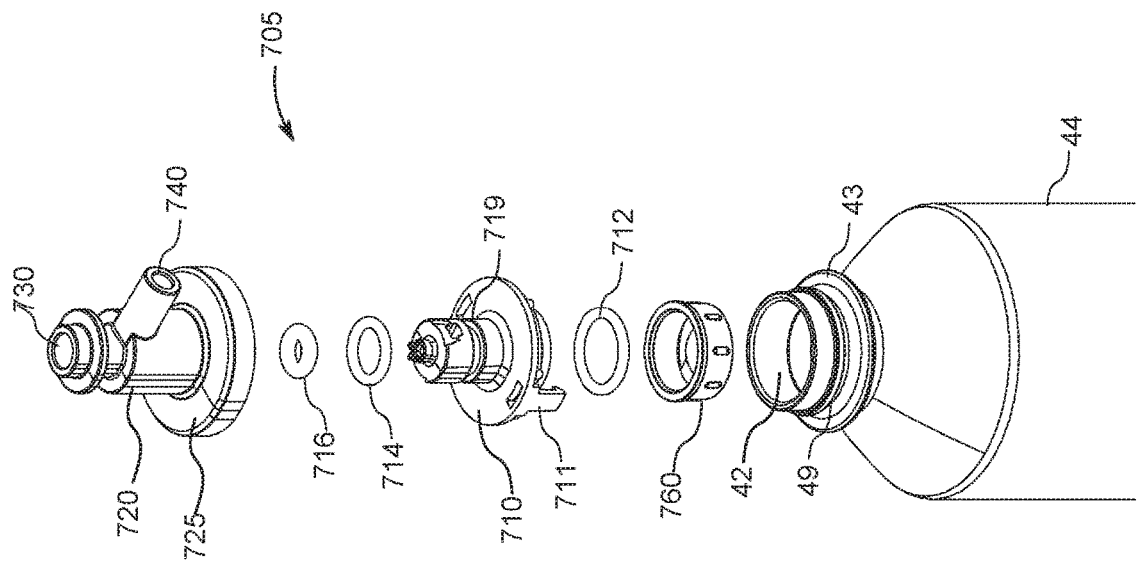
Figure 11A:
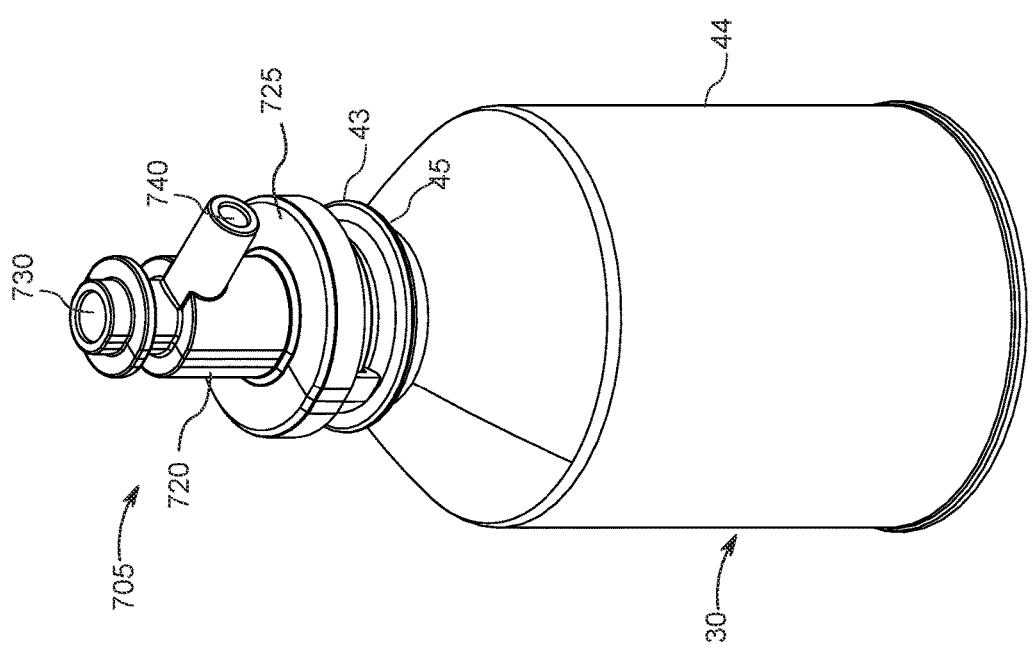

With reference to FIGS. 11A to 11F, another embodiment of a slidable syringe cap 705 is described. FIG. 11A is a top perspective view of the slidable syringe cap 705 attached to discharge neck 42 of rolling diaphragm syringe 30. Slidable syringe cap 705 includes an outer cap assembly 720 including a fluid inlet path 730 and a fluid outlet path 740. The outer cap assembly 720 also includes distal surface 725 that acts as an engagement feature to engage a corresponding cap retention feature (not shown) on a fluid injector to prevent axial distal movement of the syringe when engaged with the cap retention feature. The syringe 30 includes a flexible sidewall 44, a retention flange 43 extending around the circumferential surface of the discharge neck 42 and having a proximal surface 45 for interacting with a corresponding feature of the of the fluid injector to limit the distance that the syringe slides in the proximal direction when the end wall 34 is retracted in the proximal direction.

With reference to FIG. 11B, an exploded view of the slidable syringe cap 705 is shown. Syringe cap 705 includes the outer cap assembly 720 including a fluid inlet path 730, a fluid outlet path 740, and distal surface 725. The inner cap assembly 710 is shown which may be slidably received into a proximal end of the outer cap assembly 720 where a fluid tight seal is provided by O-ring 714 located in a circumferential groove 719 around an outer surface of the inner cap assembly 710. O-ring 716 is located at a distal end of inner cap assembly 710 and provides a fluid tight seal at the fluid inlet path 730 when the cap fluid inlet path is in the closed position. Flow diverter 760 is inserted into the discharge neck 42 of syringe 30 and may be adhesively secured or pressed friction fitted within the discharge neck 42. Inner cap assembly 710 is partially inserted into the discharge neck 42 and includes an O-ring 712 for creating a fluid tight seal between the inner surface of discharge neck 42 and the outer proximal surface of inner cap assembly 710. Inner cap assembly 710 further includes one or more clips 711 for clipping around cap securing retention flange 43 at the distal end of syringe 30 for securing the inner cap assembly to the discharge neck 42 of syringe 30.

FIGS. 11C and 11D illustrate the slidable syringe cap 705 in the first filling position where fluid communication is established between the fluid inlet path 730 and the interior of syringe 30. As shown in FIG. 11C and in detail FIG. 11D, the outer cap assembly 720 is slid distally relative to the inner cap assembly 710 and a fluid path is established through the fluid inlet path 730 around the distal end and sealing O-ring 716 of the inner cap assembly 710. Fluid then flows through inner passages 735 into the interior of the inner cap assembly 710, past the fluid diverter 760 and into the interior of syringe 30 as the proximal end wall of syringe wall 30 is drawn in the proximal direction in the fluid filling process. As the proximal end wall of syringe wall 30 is drawn in the proximal direction in the fluid filling process, the outer cap assembly 720 slides distally relative to the inner cap assembly 710 to provide fluid communication between the fluid inlet path 730 and the interior of syringe 30. A fluid tight but slidable seal between the outer cap assembly 720 and the inner cap assembly 710 by O-ring 714.

Figure 11F:
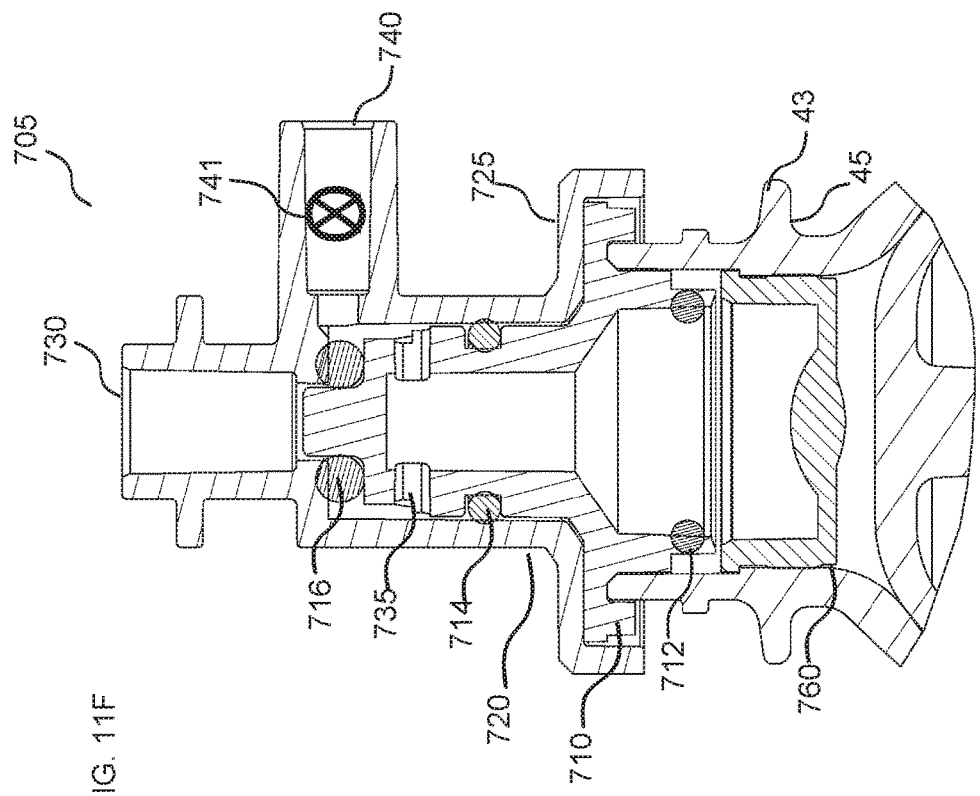
Figure 11E:
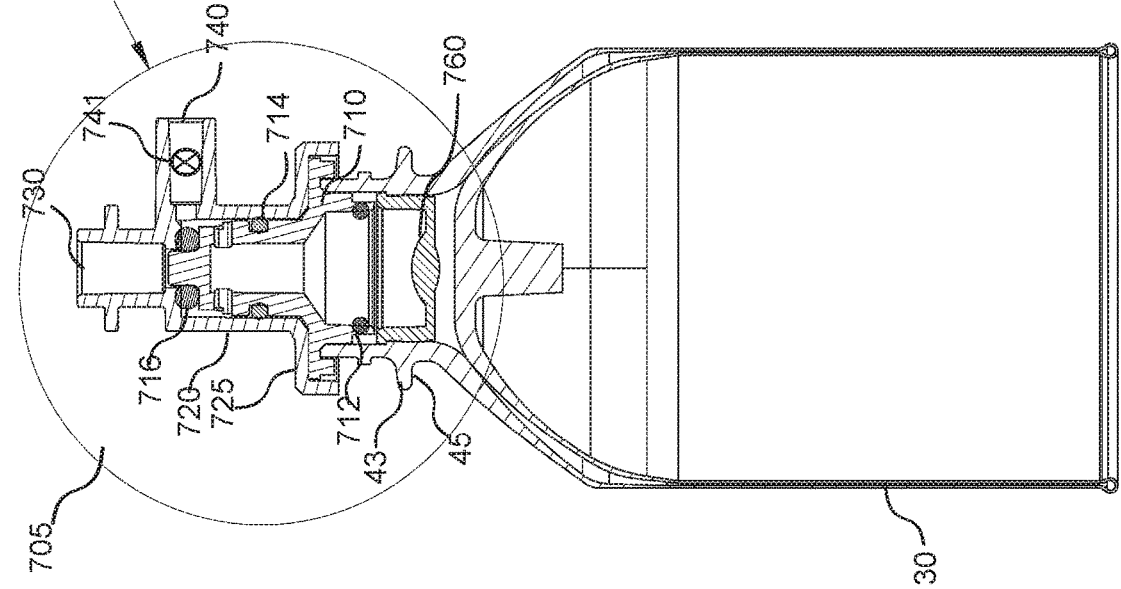

FIGS. 11E and 11F illustrate the slidable syringe cap 705 in the second delivery position where fluid communication is established between the interior of syringe 30 and the fluid outlet path 740. As shown in FIG. 11E and in detail FIG. 11F, the outer cap assembly 720 is slid proximally relative to the inner cap assembly 710 and a fluid path is established through the fluid outlet path 740. As shown in detail FIG. 11F, the distal end and sealing O-ring 716 of the inner cap assembly 710 sealably abuts a proximal surface of fluid inlet path 730 thereby preventing fluid communication between the fluid inlet path 730 and the interior of syringe 30. Fluid then flows out the fluid outlet path 740 from the interior of syringe 30, through the inner cap assembly 710, and inner passages 735 as the proximal end wall of syringe wall 30 is moved in the distal direction in the fluid delivery process. As the proximal end wall of syringe wall 30 is moved in the distal direction in the fluid delivery process, the outer cap assembly 720 slides proximally relative to the inner cap assembly 710, for example by the outer cap assembly 720 remaining axially fixed and the syringe 30 and inner cap assembly 710 assembly moving in the axial distal direction to provide fluid communication between the interior of syringe 30 and the fluid outlet path 740. Reciprocal movement of the piston results in reciprocal distal and proximal movement of the syringe 30 and inner cap assembly 710, resulting in the outer cap assembly 720 sliding proximally and distally, respectively, relative to the inner cap assembly 710, and selectively providing fluid communication between the interior of syringe 30 and fluid outlet path 740 and the fluid inlet path 730, respectively.

Figure 12C:
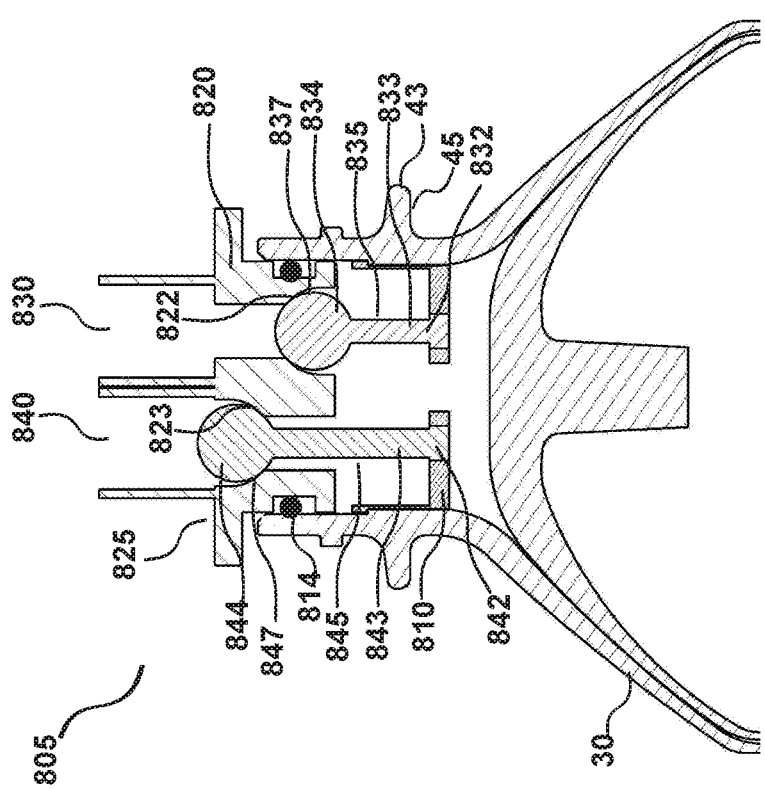

With reference to FIGS. 12A to 12C, an embodiment of a slidable syringe cap 805 is described. FIG. 12A is a side cut-away view of the slidable syringe cap 805 attached to discharge neck 42 of rolling diaphragm syringe 30. Slidable syringe cap 805 includes an outer cap assembly 820 including a fluid inlet path 830 and a fluid outlet path 840. The outer cap assembly 820 also includes distal surface 825 that acts as an engagement feature to engage a corresponding cap retention feature (not shown) on a fluid injector to prevent axial movement of the outer cap assembly 820 when engaged with the cap retention feature. The syringe 30 includes a flexible sidewall 44, a retention flange 43 extending around the circumferential surface of the discharge neck 42 and having a proximal surface 45 for interacting with a corresponding feature of the of the fluid injector to limit the distance that the syringe slides in the proximal direction when the end wall 46 is retracted in the proximal direction.

With continued reference to FIGS. 12A to 12C, slidable syringe cap 805 includes the outer cap assembly 820 and inner cap assembly 810. Inner cap assembly 810 may be received into the discharge neck 42 of syringe 30, and secured for example by friction fit, adhesive, or otherwise adhered to the inner wall of discharge neck 42. A fluid tight but slidable seal between the outer cap assembly 820 and the inner cap assembly 810 by O-ring 814. A flow diverter (not shown in FIG. 12A to 12C) is inserted into the discharge neck 42 of syringe 30 and may be adhesively secured within the discharge neck 42. Inner cap assembly 810 is inserted into the discharge neck 42 and creates a tight seal, for example by adhesive or friction fit, between the inner surface of discharge neck 42 and the outer proximal surface of inner cap assembly 810.

FIG. 12A illustrates the slidable syringe cap 805 in the first filling position where fluid communication is established between the fluid inlet path 830 and the interior of syringe 30. Inner cap assembly includes an inlet closure member 835 and an outlet closure member 845. The inlet closure member 835 includes a first portion 834 having a sealing surface 837 for creating a fluid tight sealing engagement with the sealing surface 822 of the fluid inlet path 830. As shown in FIG. 12A, there is no fluid tight seal between the sealing surface 837 and sealing surface 822 of the fluid inlet path 830. Inlet closure member 835 further includes elastic connector member 833 and second portion 832 connected to the inner cap assembly 810. As shown in the FIG. 12A, the elastic connector member 833 is in the relaxed position when not in the closed position. The outlet closure member 845 includes a first portion 844 having a sealing surface 847 for creating a fluid tight sealing engagement with the sealing surface 823 of the fluid outlet path 840. As shown in FIG. 12A, there is a fluid tight seal between the sealing surface 847 and sealing surface 823 of the fluid outlet path 840. Outlet closure member 845 further includes elastic connector member 843 and second portion 842 connected to the inner cap assembly 810. As shown in the FIG. 12A, the elastic connector member 843 is in the stretched position when in the closed position, where stretched elastic connector member 843 pulls the sealing surface 847 of the first portion 844 against sealing surface 823 of the fluid outlet path 840.

As shown in FIG. 12A, the outer cap assembly 820 is slid distally relative to the inner cap assembly 810 and a fluid path is established through the fluid inlet path 830 around the first portion 834 and sealing surfaces 837 and 822 of the inlet closure member 835. Fluid then flows into the interior of the inner cap assembly 810, past the fluid diverter (not shown) and into the interior of syringe 30 as the proximal end wall of syringe wall 30 is drawn in the proximal direction in the fluid filling process. As the proximal end wall of syringe wall 30 is drawn in the proximal direction in the fluid filling process, the outer cap assembly 820 slides distally relative to the inner cap assembly 810 to provide fluid communication between the fluid inlet path 830 and the interior of syringe 30. Concurrently, as the outer cap assembly 820 slides distally relative to the inner cap assembly 810, the elastic connector member 843 of the outlet closure member 845 stretches and pulls the sealing surface 847 of first portion 844 into a fluid tight seal against the sealing surface 823 of the fluid outlet path 840.

FIG. 12B illustrates the slidable syringe cap 805 in the first delivery position where fluid communication is established between the fluid outlet path 840 and the interior of syringe 30 as the outer cap assembly 820 is moved in the proximal direction relative to the inner cap assembly 810. As shown in FIG. 12B, the inlet closure member 835 is in the closed position as a fluid tight seal is formed between the sealing surface 837 and sealing surface 822 of the fluid inlet path 830. The seal results as elastic connector member 833 is in the compressed forcing the sealing surface 837 against sealing surface 822 of the fluid inlet path 830. As shown in FIG. 12B, there is no seal between the sealing surface 847 and sealing surface 823 of the fluid outlet path 840 as the elastic connector member 843 of the outlet closure member 845 is in the relaxed position and does not pull the sealing surface 847 of the first portion 844 against sealing surface 823 of the fluid outlet path 840.

As shown in FIG. 12B, as outer cap assembly 820 is slid proximally relative to the inner cap assembly 810 and a fluid path is established through the fluid outlet path 840. Fluid flows past the elastic connector member 843 from the interior of the inner cap assembly 810, around the first portion 844 and sealing surfaces 847 and 823 of the outlet closure member 845 and into the fluid outlet valve 840. As the proximal end wall of syringe wall 30 is moved in the distal direction in the fluid delivery process, the outer cap assembly 820 slides proximally relative to the inner cap assembly 810 to provide fluid communication between the fluid outlet path 840 and the interior of syringe 30. Concurrently, as the outer cap assembly 820 slides proximally relative to the inner cap assembly 810, the elastic connector member 833 of the inlet closure member 835 compresses and pushes the sealing surface 837 of first portion 834 into a fluid tight seal against the sealing surface 822 of the fluid inlet path 830.

FIG. 12C illustrates the slidable syringe cap 805 in a third closed position where fluid communication is blocked between the fluid outlet path 840 and the interior of syringe 30 and between the fluid inlet path 830 and the interior of the syringe 30. As shown in FIG. 12C, the inlet closure member 835 is in the closed position as a fluid tight seal is formed between the sealing surface 837 and sealing surface 822 of the fluid inlet path 830. Further, the outlet closure member 845 is also in the closed position as a fluid tight seal is formed between the sealing surface 847 and sealing surface 823 of the fluid outlet path 840. As shown in FIG. 12C, the third closed position has the outer cap assembly 820 at a position slidably located relative to the inner cap assembly 810 between the first filling position and the second delivery position.

Figure 13A:
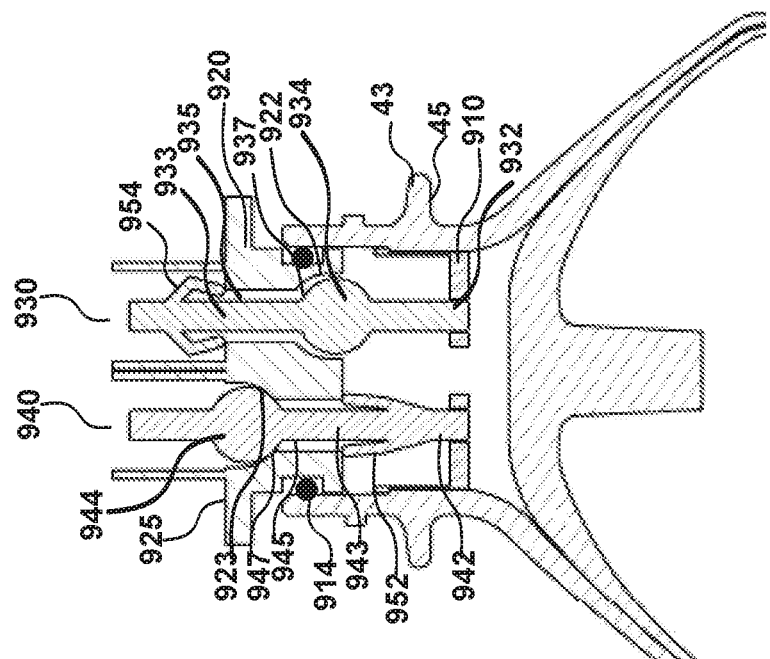
FIGS. 13A to 13C illustrate an embodiment of the syringe cap including a fluid inlet closure member and an outlet closure member in the fill position FIG. 13A, the delivery position FIG. 13B, and in the closed position FIG. 13C.
Figure 13C:
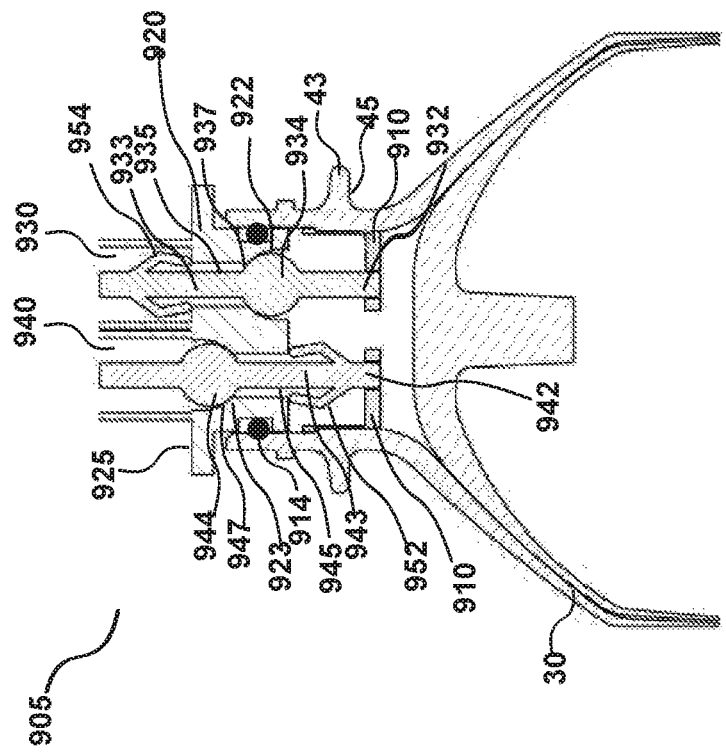
Figure 13B:
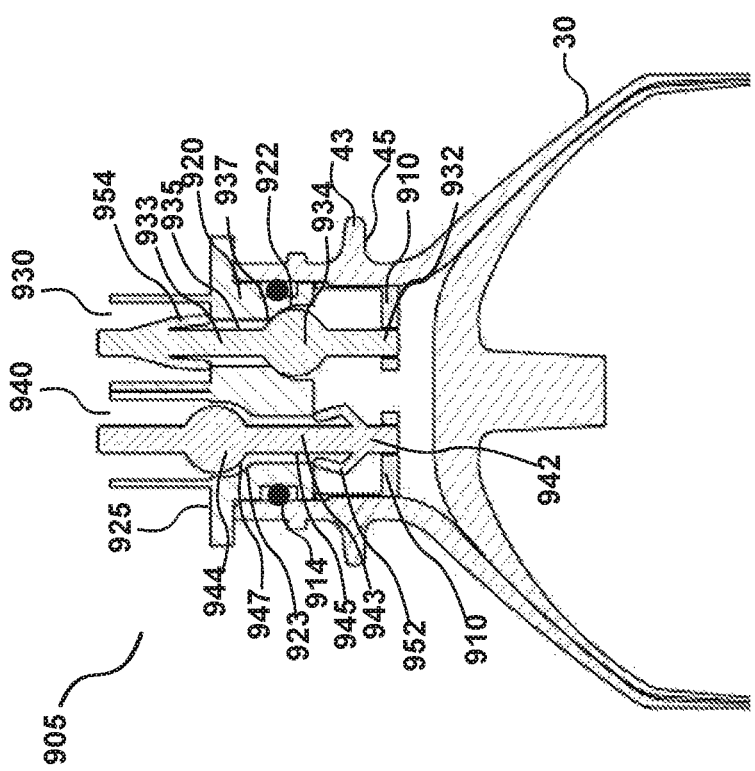

With reference to FIGS. 13A to 13C, an embodiment of a slidable syringe cap 905 is described. FIG. 13A is a side cut-away view of the slidable syringe cap 905 attached to discharge neck 42 of rolling diaphragm syringe 30. Slidable syringe cap 905 includes an outer cap assembly 920 including a fluid inlet path 930 and a fluid outlet path 940. The outer cap assembly 920 also includes distal surface 925 that acts as an engagement feature to engage a corresponding cap retention feature (not shown) on a fluid injector to prevent axial movement of the outer cap assembly 920 when engaged with the cap retention feature. The syringe 30 includes a flexible sidewall 44, a retention flange 43 extending around the circumferential surface of the discharge neck 42 and having a proximal surface 45 for interacting with a corresponding feature of the of the fluid injector to limit the distance that the syringe slides in the proximal direction when the end wall 46 is retracted in the proximal direction.

With continued reference to FIGS. 13A to 13C, slidable syringe cap 905 includes the outer cap assembly 920 and inner cap assembly 910. Inner cap assembly 910 may be received into the discharge neck 42 of syringe 30, and secured for example by friction fit, adhesive, or otherwise adhered to the inner wall of discharge neck 42. A fluid tight but slidable seal between the outer cap assembly 920 and the inner cap assembly 910 by O-ring 914. A flow diverter (not shown in FIG. 13A to 13C) is inserted into the discharge neck 42 of syringe 30 and may be adhesively secured within the discharge neck 42. Inner cap assembly 910 is inserted into the discharge neck 42 and creates a tight seal, for example by adhesive or friction fit, between the inner surface of discharge neck 42 and the outer proximal surface of inner cap assembly 910.

FIG. 13A illustrates the slidable syringe cap 905 in the first filling position where fluid communication is established between the fluid inlet path 930 and the interior of syringe 30. Inner cap assembly includes an inlet closure member 935 and an outlet closure member 945. Each of the inlet closure member 935 and the outlet closure member 945 include a plurality of bendable legs 954 and 952, respectively, extending from the second portions 932 of the inlet closure member 935 and the second portion 942 of the outlet closure member 945. The plurality of bendable legs 954 of the inlet closure member 935 are attached at a first leg end to the inlet closure member 935 and have a second leg end that abuts a distal surface in the fluid inlet path 930 and further have a flexible bend portion located between the first portion and the second portion. In the open position for the inlet closure member 935, the plurality of legs 954 are in the bent configuration. The inlet closure member 935 includes a first portion 934 having a sealing surface 937 for creating a fluid tight sealing engagement with the sealing surface 922 of the fluid inlet path 930. As shown in FIG. 13A, there is no fluid tight seal between the sealing surface 937 and sealing surface 922 of the fluid inlet path 930. Inlet closure member 935 further includes elastic connector member 933 and second portion 932 connected to the inner cap assembly 910. As shown in the FIG. 13A, the elastic connector member 933 is in the relaxed position when not in the closed position. The outlet closure member 945 includes a first portion 944 having a sealing surface 947 for creating a fluid tight sealing engagement with the sealing surface 923 of the fluid outlet path 940. The plurality of bendable legs 952 of the outlet closure member 945 are attached at a first leg end to the outlet closure member 945 and have a second leg end that abuts a proximal surface in the outer cap assembly 920 and further have a flexible bend portion located between the first portion and the second portion. As shown in FIG. 13A, there is a fluid tight seal between the sealing surface 947 and sealing surface 923 of the fluid outlet path 940. Outlet closure member 945 further includes elastic connector member 943 and second portion 942 connected to the inner cap assembly 910. As shown in the FIG. 13A, the plurality of bendable legs 952 are in a relaxed position when in the closed position, where elastic connector member 943 is configured to place the sealing surface 947 of the first portion 944 against sealing surface 923 of the fluid outlet path 940.

As shown in FIG. 13A, the outer cap assembly 920 is slid distally relative to the inner cap assembly 910 and a fluid path is established through the fluid inlet path 930, through the plurality of legs 954, around the first portion 934 and sealing surfaces 937 and 922 of the inlet closure member 935. Fluid then flows into the interior of the inner cap assembly 910, past the fluid diverter (not shown) and into the interior of syringe 30 as the proximal end wall of syringe wall 30 is drawn in the proximal direction in the fluid filling process. As the proximal end wall of syringe wall 30 is drawn in the proximal direction in the fluid filling process, the plurality of bendable legs 954 on the inlet closure member 935 are relaxed, the outer cap assembly 920 slides distally relative to the inner cap assembly 910 to provide fluid communication between the fluid inlet path 930 and the interior of syringe 30. Concurrently, as the outer cap assembly 920 slides distally relative to the inner cap assembly 910, the elastic connector member 943 of the outlet closure member 945 at least partially stretches and pulls the sealing surface 947 of first portion 944 into a fluid tight seal against the sealing surface 923 of the fluid outlet path 940.

FIG. 13B illustrates the slidable syringe cap 905 in the first delivery position where fluid communication is established between the fluid outlet path 940 and the interior of syringe 30 as the outer cap assembly 920 is moved in the proximal direction relative to the inner cap assembly 910. As shown in FIG. 13B, the inlet closure member 935 is in the closed position as a fluid tight seal is formed between the sealing surface 937 and sealing surface 922 of the fluid inlet path 930 while the associated plurality of bendable legs 954 are moved to the relaxed position. The seal results as elastic connector member 933 is in the compressed forcing the sealing surface 937 against sealing surface 922 of the fluid inlet path 930. As shown in FIG. 13B, for the outlet fluid path 940, the plurality of bendable legs 952 are in the bent configuration and there is no seal between the sealing surface 947 and sealing surface 923 of the fluid outlet path 940 as the elastic connector member 943 of the outlet closure member 945 is in the relaxed position and does not pull the sealing surface 947 of the first portion 944 against sealing surface 923 of the fluid outlet path 940.

As shown in FIG. 13B, the outer cap assembly 920 is slid proximally relative to the inner cap assembly 910 and a fluid path is established through the fluid outlet path 940. Fluid flows past the bendable legs 952 from the interior of the inner cap assembly 910, around the first portion 944 and sealing surfaces 947 and 923 of the outlet closure member 945 and into the fluid outlet valve 940. As the proximal end wall of syringe wall 30 is moved in the distal direction in the fluid delivery process, the outer cap assembly 920 slides proximally relative to the inner cap assembly 910 to provide fluid communication between the fluid outlet path 940 and the interior of syringe 30. Concurrently, as the outer cap assembly 920 slides proximally relative to the inner cap assembly 910, the plurality of bendable legs 954 relax and the elastic connector member 933 of the inlet closure member 935 compresses and pushes the sealing surface 937 of first portion 934 into a fluid tight seal against the sealing surface 922 of the fluid inlet path 930.

FIG. 13C illustrates the slidable syringe cap 905 in a third closed position where fluid communication is blocked between the fluid outlet path 940 and the interior of syringe 30 and between the fluid inlet path 930 and the interior of the syringe 30. As shown in FIG. 13C, the inlet closure member 935 is in the closed position as a fluid tight seal is formed between the sealing surface 937 and sealing surface 922 of the fluid inlet path 930. Further, the outlet closure member 945 is also in the closed position as a fluid tight seal is formed between the sealing surface 947 and sealing surface 923 of the fluid outlet path 940. As shown in FIG. 13C, the third closed position has the outer cap assembly 920 at a position slidably located relative to the inner cap assembly 910 between the first filling position and the second delivery position.

Figure 14C:
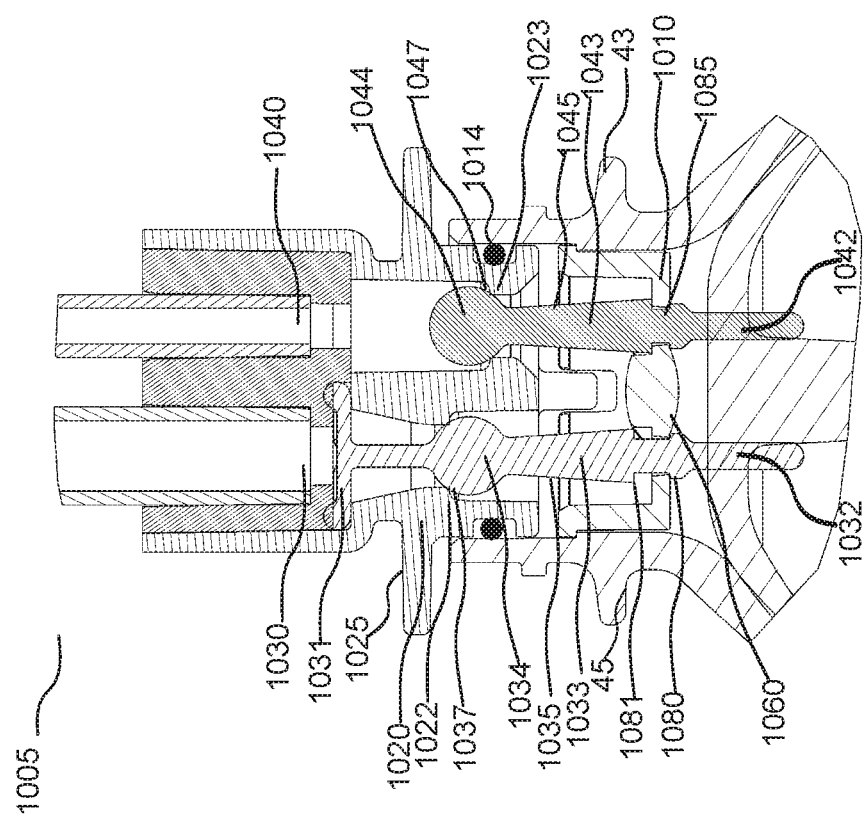

With reference to FIGS. 14A to 14C, an embodiment of a slidable syringe cap 1005 is described. FIG. 14A is a side cut-away view of the slidable syringe cap 1005 attached to discharge neck 42 of rolling diaphragm syringe 30. Slidable syringe cap 1005 includes an outer cap assembly 1020 including a fluid inlet path 1030 and a fluid outlet path 1040. The outer cap assembly 1020 also includes distal surface 1025 that acts as an engagement feature to engage a corresponding cap retention feature (not shown) on a fluid injector to prevent axial movement of the outer cap assembly 1020 when engaged with the cap retention feature. The syringe 30 includes a flexible sidewall 44, a retention flange 43 extending around the circumferential surface of the discharge neck 42 and having a proximal surface 45 for interacting with a corresponding feature of the of the fluid injector to limit the distance that the syringe slides in the proximal direction when the end wall 46 is retracted in the proximal direction.

With continued reference to FIGS. 14A to 14C, slidable syringe cap 1005 includes the outer cap assembly 1020 and inner cap assembly 1010. Inner cap assembly 1010 may be received into the discharge neck 42 of syringe 30, and secured for example by friction fit, adhesive, or otherwise adhered to the inner wall of discharge neck 42. A fluid tight but slidable seal is formed between the outer cap assembly 1020 and the inner cap assembly 1010 by O-ring 1014. A flow diverter 1060, which may be integrated into the inner cap assembly 1010, is inserted into the discharge neck 42 of syringe 30 and may be adhesively secured within the discharge neck 42. Inner cap assembly 1010 is inserted into the discharge neck 42 and creates a fluid tight seal, for example by adhesive or friction fit, between the inner surface of discharge neck 42 and the outer proximal surface of inner cap assembly 1010.

FIG. 14A illustrates the slidable syringe cap 1005 in the first filling position where fluid communication is established between the fluid inlet path 1030 and the interior of syringe 30. Inner cap assembly includes an inlet closure member 1035 and an outlet closure member 1045. The inlet closure member 1035 includes a first portion 1034 having a sealing surface 1037 for creating a fluid tight sealing engagement with the sealing surface 1022 of the fluid inlet path 1030 and further includes a biasing spring member 1031 in tension when the inlet closure member is in the open position. Biasing spring member 1031 can be in spring tension while still allowing fluid flow through a plurality of flow paths (not shown) through a surface thereof. As the syringe 30 and inner cap assembly 1010 are moved in the proximal direction, the inner cap assembly 1010 slides proximally relative to the outer cap assembly 1020 and ledge 1080 at the second portion 1032 of the inlet closure member 1035 engages the inner cap assembly 1010 and draws the inlet closure member in the proximal direction against the biasing force of the biasing spring member 1031. As shown in FIG. 14A, there is no fluid tight seal between the sealing surface 1037 and sealing surface 1022 of the fluid inlet path 1030. Inlet closure member 1035 further includes elastic connector member 1033 and second portion 1032 connected to the inner cap assembly 1010. As shown in the FIG. 14A, the elastic connector member 1033 is in the substantially relaxed position when not in the closed position except against the tension provided by the biasing spring member 1031. The outlet closure member 1045 includes a first portion 1044 having a sealing surface 1047 for creating a fluid tight sealing engagement with the sealing surface 1023 of the fluid outlet path 1040. As shown in FIG. 14A, there is a fluid tight seal between the sealing surface 1047 and sealing surface 1023 of the fluid outlet path 1040. Outlet closure member 1045 further includes elastic connector member 1043 and second portion 1042 connected to the inner cap assembly 1010. As shown in the FIG. 14A, the elastic connector member 1043 is in the stretched position when in the closed position, where stretched elastic connector member 1043 pulls the sealing surface 1047 of the first portion 1044 against sealing surface 1023 of the fluid outlet path 1040.

As shown in FIG. 14A, the outer cap assembly 1020 is slid distally relative to the inner cap assembly 1010 and a fluid path is established through the fluid inlet path 1030 and the plurality of flow paths in the biasing spring member 1031, around the first portion 1034 and sealing surfaces 1037 and 1022 of the inlet closure member 1035. Fluid then flows into the interior of the inner cap assembly 1010, past the fluid diverter 1060 and into the interior of syringe 30 as the proximal end wall of syringe wall 30 is drawn in the proximal direction in the fluid filling process. As the proximal end wall of syringe wall 30 is drawn in the proximal direction in the fluid filling process, the outer cap assembly 1020 slides distally relative to the inner cap assembly 1010 to provide fluid communication between the fluid inlet path 1030 and the interior of syringe 30. Concurrently, as the outer cap assembly 1020 slides distally relative to the inner cap assembly 1010, the elastic connector member 1043 of the outlet closure member 1045 stretches and pulls the sealing surface 1047 of first portion 1044 into a fluid tight seal against the sealing surface 1023 of the fluid outlet path 1040.

FIG. 14B illustrates the slidable syringe cap 1005 in the first delivery position where fluid communication is established between the fluid outlet path 1040 and the interior of syringe 30 as the outer cap assembly 1020 is moved in the proximal direction relative to the inner cap assembly 1010. As shown in FIG. 14B, the inlet closure member 1035 is in the closed position as a fluid tight seal is formed between the sealing surface 1037 and sealing surface 1022 of the fluid inlet path 1030. The seal results as elastic connector member 1033 is in the compressed state forcing the sealing surface 1037 against sealing surface 1022 of the fluid inlet path 1030 by the inner cap assembly 1010 sliding in the distal direction and engaging opposite ledge 1081 of the inlet closure member 1035, in combination with the relaxation of the biasing spring member 1031. As shown in FIG. 14B, there is no seal between the sealing surface 1047 and sealing surface 1023 of the fluid outlet path 1040 as the elastic connector member 1043 of the outlet closure member 1045 is moved in the distal direction as a result of the engagement of groove 1085 and the inner cap assembly such that the outlet closure member 1045 is in the relaxed position and does not pull the sealing surface 1047 of the first portion 1044 against sealing surface 1023 of the fluid outlet path 1040.

As shown in FIG. 14B, as outer cap assembly 1020 is slid proximally relative to the inner cap assembly 1010 and a fluid path is established through the fluid outlet path 1040. Fluid flows past the elastic connector member 1043 from the interior of the inner cap assembly 1010, around the first portion 1044 and sealing surfaces 1047 and 1023 of the outlet closure member 1045 and into the fluid outlet valve 1040. As the proximal end wall of syringe wall 30 is moved in the distal direction in the fluid delivery process, the outer cap assembly 1020 slides proximally relative to the inner cap assembly 1010 to provide fluid communication between the fluid outlet path 1040 and the interior of syringe 30. Concurrently, as the outer cap assembly 1020 slides proximally relative to the inner cap assembly 1010, the elastic connector member 1033 of the inlet closure member 1035 compresses and pushes the sealing surface 1037 of first portion 1034 into a fluid tight seal against the sealing surface 1022 of the fluid inlet path 1030.

FIG. 14C illustrates the slidable syringe cap 1005 in a third closed position where fluid communication is blocked between the fluid outlet path 1040 and the interior of syringe 30 and between the fluid inlet path 1030 and the interior of the syringe 30. As shown in FIG. 14C, the inlet closure member 1035 is in the closed position as a fluid tight seal is formed between the sealing surface 1037 and sealing surface 1022 of the fluid inlet path 1030 which may be due, at least in part, by the biasing force provided by the biasing spring member 1031. Further, the outlet closure member 1045 is also in the closed position as a fluid tight seal is formed between the sealing surface 1047 and sealing surface 1023 of the fluid outlet path 1040. As shown in FIG. 14C, the third closed position has the outer cap assembly 1020 at a position slidably located relative to the inner cap assembly 1010 between the first filling position and the second delivery position.

Figure 15:
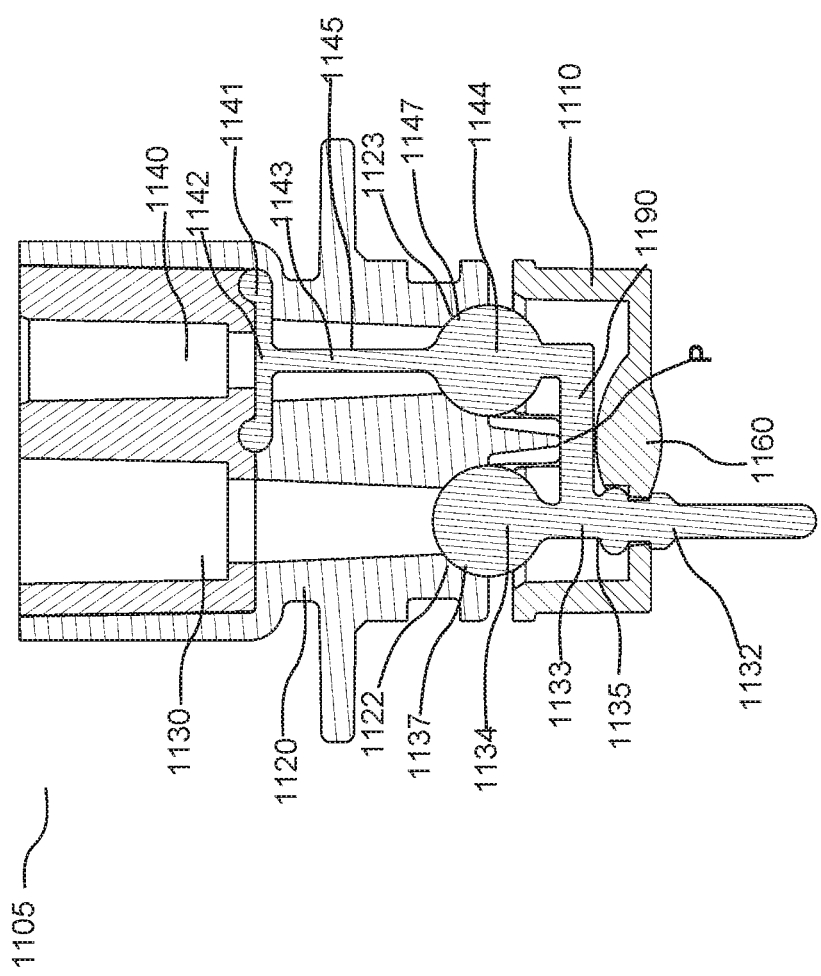
FIG. 15 illustrates an embodiment of the syringe cap including a fluid inlet closure member and an outlet closure member according to an embodiment.

FIG. 15 illustrates the sliding syringe cap 1105 having a levered fluid control apparatus that moves between the first filling position where fluid communication is established between the fluid inlet path 1130 and the interior of syringe 30 and the second delivery position where fluid communication is established between the fluid outlet path 1140 and the interior of syringe 30. Inner cap assembly 1110 includes an inlet closure member 1135 and an outlet closure member 1145 connected by a levered crossbar 1190 that rotates around a pivot point P to selectively open the fluid inlet path 1130 or the fluid outlet path 1140. In certain embodiments, the sliding syringe cap may include a third closed position where the fluid inlet path 1130 and the fluid outlet path 1140 are fluidly isolated from the interior of syringe 30, for example where both the inlet closure member 1135 and the outlet closure member 1145 are in the closed position. The inlet closure member 1135 includes a first portion 1134 having a sealing surface 1137 for creating a fluid tight sealing engagement with the sealing surface 1122 of the fluid inlet path 1130. As the syringe 30 and inner cap assembly slide 1110 in the proximal direction relative to the outer cap assembly 1120, the inlet closure member 1135 which moves the first portion 1134 away from sealing surface 1122, bringing the fluid inlet path 1130 into fluid communication with the interior of syringe 30. Inlet closure member 1135 further includes elastic connector member 1133 and second portion 1132 which interacts with the inner cap assembly 1110. The outlet closure member 1145 includes a first portion 1144 having a sealing surface 1147 for creating a fluid tight sealing engagement with the sealing surface 1123 of the fluid outlet path 1140 and further includes a biasing spring member 1141 in tension when the inlet closure member 1145 is in the open position. Biasing spring member 1141 is located at the second position 1142 and can be in spring tension while still allowing fluid flow through a plurality of flow paths (not shown) through a surface thereof. As syringe 30 and inner cap assembly 1110 are moved in the distal direction, the inner cap assembly 1110 slides distally relative to the outer cap assembly 1120 and the inlet closure member 1135 engages the inner cap assembly 1110. The elastic connector member 1133 is elastic and can compress/bend under the compression from the distal movement of the inner cap assembly 1110 and causes levered cross bar 1190 to move the outlet closure member 1145 in the proximal direction disengaging sealing surface 1147 from sealing surface 1123 allowing fluid communication between the fluid outlet path 1140 and the interior of the syringe 30. Simultaneously, inlet closure member 1135 is moved in the distal direction causing a sealing engagement between sealing surface 1137 and 1122 to prevent fluid communication between the fluid inlet path 1130 and the interior of the syringe 30. In the absence of the levering force on outlet closure member 1145, the biasing force of the biasing spring member 1141 biases the outlet closure member 1145 back to the fluidly sealed arrangement. As shown in FIG. 15, the levered embodiment of the sliding syringe cap may have a third closed position where inlet closure member 1135 is in a sealing engagement between sealing surface 1137 and 1122 and outlet closure member 1145 is in a sealing engagement between sealing surface 1147 and 1123.

The present disclosure has been described with reference to specific details of specific examples thereof. It is not intended that such details be regarded as limitations upon the scope of the disclosure.

We claim:

1. A cap for intake and delivery of a liquid fluid from a syringe, the cap comprising:
   an outer cap assembly comprising a fluid inlet path and a fluid outlet path; and
   an inner cap assembly configured for insertion into a fluid nozzle of the syringe and to provide selective fluid communication between an interior of the syringe and the fluid inlet path or the fluid outlet path,
   wherein the outer cap assembly is slidable relative to the inner cap assembly and the syringe between a first filling position, where the interior of the syringe is in fluid communication with the fluid inlet path, and a second delivery position, where the interior of the syringe is in fluid communication with the fluid outlet path,
   wherein the outer cap assembly has an engagement surface configured to engage a cap retention element of a fluid injector, wherein a cap engagement surface on the cap retention element prevents movement of the outer cap assembly in at least one of a proximal direction and a distal direction when the engagement surface on the outer cap assembly is engaged with the cap retention element, and
   wherein, when the engagement surface engages the cap retention element of the fluid injector, the outer cap assembly is slidable relative to the inner cap assembly upon distal and proximal movement of the syringe having the cap attached thereto.

2. The cap of claim 1, wherein the inner cap assembly further comprises a flow controller to divert flow of the liquid fluid to an inner wall of the syringe when the syringe is being filled with the liquid fluid.

3. The cap of claim 1, wherein the cap is in the first filling position when one of a plunger and a proximal end wall of the syringe is drawn in the proximal direction by a piston of the fluid injector.

4. The cap of claim 1, wherein the cap is in the second delivery position when one of a plunger and a proximal end wall of the syringe is pushed in the distal direction by a piston of the fluid injector.

5. The cap of claim 1, wherein the cap slides between the first filling position and the second delivery position when a direction of movement of a plunger or a proximal end wall of the syringe is changed from the proximal direction to the distal direction.

6. The cap of claim 1, wherein at least one of the fluid inlet path and the fluid outlet path includes a closure member configured to move between a closed position and an open position upon sliding of the outer cap assembly relative to the inner cap assembly.

7. The cap of claim 6, wherein the closure member comprises:
   a first portion having a sealing surface for creating a fluid tight seal with a surface associated with the at least one of the fluid inlet path and the fluid outlet path when the closure member is in the closed position;
   a second portion; and
   an elastic connector member between the first portion and the second portion, wherein the elastic connector member connects the closure member to the inner cap assembly,
   wherein the elastic connector member is configured to at least one of stretch, compress, and bend as the closure member moves between the open position and the closed position.

8. The cap of claim 7, wherein the elastic connector member comprises a plurality of bendable legs connecting the elastic connector member to the inner cap assembly, and wherein the plurality of bendable legs bend as the closure member moves between the open position and the closed position.

9. The cap of claim 1, wherein the fluid inlet path comprises an inlet closure member and the fluid outlet path comprises an outlet closure member,
   wherein the inlet closure member is in an open position when the syringe is being filled with the liquid fluid and in a closed position when the syringe is delivering the liquid fluid, and
   wherein the outlet closure member is in a closed position when the syringe is being filled with the liquid fluid and in an open position when the syringe is delivering the liquid fluid.

10. The cap of claim 1, wherein the outer cap assembly is slidable relative to the inner cap assembly to a third closed position where there is no fluid communication between the interior of the syringe and the fluid inlet path or the fluid outlet path.

11. A syringe for a fluid injector, the syringe comprising:
    a proximal end, a distal end, and a cylindrical sidewall between the proximal end and the distal end defining an interior volume for retaining a medical fluid therein;
    a fluid nozzle at the distal end;
    a piston engagement feature located on one of a plunger slidably associated with the syringe and a proximal end wall of the syringe, the piston engagement feature configured for releasably engaging a piston of the fluid injector; and
    a cap at least partially inserted into the fluid nozzle and configured to intake and deliver of the medical fluid from the syringe, the cap comprising:
       an outer cap assembly comprising a fluid inlet path and a fluid outlet path; and
       an inner cap assembly configured for insertion into the fluid nozzle of the syringe and to provide selective fluid communication between an interior of the syringe and the fluid inlet path or the fluid outlet path,
       wherein the outer cap assembly is slidable relative to the inner cap assembly and the fluid nozzle of the syringe between a first filling position, where the interior of the syringe is in fluid communication with the fluid inlet path, and a second delivery position, where the interior of the syringe is in fluid communication with the fluid outlet path,
       wherein the outer cap assembly has an engagement surface configured to engage a cap retention element of the fluid injector, wherein a cap engagement surface on the cap retention element prevents movement of the outer cap assembly in at least one of a proximal direction and a distal direction when the engagement surface on the outer cap assembly is engaged with the cap retention element, and
       wherein, when the engagement surface engages the cap retention element of the fluid injector, the outer cap assembly is slidable relative to the inner cap assembly upon distal and proximal movement of the syringe having the cap attached thereto.

12. The syringe of claim 11, the syringe further comprising a retention flange having a proximal surface that limits a distance that the syringe slides in the proximal direction when the plunger or the proximal end wall is retracted in the proximal direction.

13. The syringe of claim 11, wherein the cap is in the first filling position when one of the plunger and the proximal end wall of the syringe is drawn in the proximal direction by the piston of the fluid injector.

14. The syringe of claim 11, wherein the cap is in the second delivery position when one of the plunger and the proximal end wall of the syringe is pushed in the distal direction by the piston of the fluid injector.

15. The syringe of claim 11, wherein the cap slides between the first filling position and the second delivery position when a direction of movement of the plunger or the proximal end wall of the syringe is changed from the proximal direction to the distal direction.

16. The syringe of claim 11, wherein the outer cap assembly is slidable relative to the inner cap assembly to a third closed position where there is no fluid communication between the interior of the syringe and the fluid inlet path or the fluid outlet path.

* * * * *

UNITED STATES PATENT AND TRADEMARK OFFICE
CERTIFICATE OF CORRECTION

| | | |
|---|---|---|
| PATENT NO. | : 11,826,541 B2 | |
| APPLICATION NO. | : 16/621809 | |
| DATED | : November 28, 2023 | |
| INVENTOR(S) | : Cowan et al. | |

It is certified that error appears in the above-identified patent and that said Letters Patent is hereby corrected as shown below:

On the Title Page

(72) SEVENTH INVENTOR'S NAME, delete "Joseph Ranaletta" and insert -- "Joseph Ranalletta" --, therefor.

In the Specification

In Column 1, below title insert -- CROSS REFERENCE TO RELATED APPLICATIONS --.
In Column 8, Line 62, delete "onto,." and insert -- onto. --, therefor.
In Column 10, Line 34, delete "size" and insert -- sized --, therefor.
In Column 17, Lines 22-23, delete "described in described in" and insert -- described in --, therefor.
In Column 17, Line 48, delete "the a" and insert -- the --, therefor.
In Column 18, Line 24, delete "compatibility" and insert -- compatibility. --, therefor.
In Column 21, Line 10, delete "a" and insert -- to a --, therefor.
In Column 24, Line 36, delete "of the of the" and insert -- of the --, therefor.
In Column 25, Line 57, delete "of the of the" and insert -- of the --, therefor.
In Column 27, Line 53, delete "of the of the" and insert -- of the --, therefor.
In Column 30, Line 3, delete "of the of the" and insert -- of the --, therefor.

In the Claims

In Column 34, Line 42, delete "and deliver of" and insert -- and deliver --, therefor.

Signed and Sealed this
Fifth Day of March, 2024

Katherine Kelly Vidal
*Director of the United States Patent and Trademark Office*